United States Patent
Shim et al.

(10) Patent No.: US 10,583,062 B2
(45) Date of Patent: Mar. 10, 2020

(54) JOINT ASSEMBLY AND MOTION ASSISTANCE DEVICE COMPRISING THE JOINT ASSEMBLY

(71) Applicant: Samsung Electronics Co., Ltd., Suwon-si, Gyeonggi-do (KR)

(72) Inventors: Youngbo Shim, Seoul (KR); Jongwon Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 870 days.

(21) Appl. No.: 15/155,394

(22) Filed: May 16, 2016

(65) Prior Publication Data
US 2017/0119615 A1 May 4, 2017

(30) Foreign Application Priority Data
Nov. 4, 2015 (KR) .................. 10-2015-0154621

(51) Int. Cl.
*A61H 3/00* (2006.01)
*A61H 1/02* (2006.01)
(Continued)

(52) U.S. Cl.
CPC .............. *A61H 3/00* (2013.01); *A61F 2/70* (2013.01); *A61F 2/72* (2013.01); *A61H 1/024* (2013.01); *A61H 1/0244* (2013.01); *A61H 1/0262* (2013.01); *A61H 1/0266* (2013.01); *A61H 1/0274* (2013.01); *A61H 1/0277* (2013.01); *A61H 1/0281* (2013.01); *A61H 1/0285* (2013.01); *A61F 2002/701* (2013.01); *A61H 2201/1215* (2013.01); *A61H 2201/1261* (2013.01); *A61H 2201/14* (2013.01); *A61H 2201/1418* (2013.01); *A61H 2201/163* (2013.01); *A61H 2201/165* (2013.01);
(Continued)

(58) Field of Classification Search
CPC .................................. F16C 11/12; A61F 2/68
See application file for complete search history.

(56) References Cited

U.S. PATENT DOCUMENTS 6,666,283 B2 * 12/2003 Frauhammer ......... B25B 23/141
173/93
2004/0224275 A1 * 11/2004 Lonardi .................... C21B 7/20
432/100
(Continued)

FOREIGN PATENT DOCUMENTS

EP  0 254 897 A1  2/1988
EP  2 932 953 A1  10/2015
(Continued)

OTHER PUBLICATIONS

Extended European Search Report issued by the European Patent Office dated Mar. 9, 2017 for the corresponding EP Patent Application No. 16197111.4.

*Primary Examiner* — Yashita Sharma
(74) *Attorney, Agent, or Firm* — Harness, Dickey & Pierce, P.L.C.

(57) ABSTRACT

A joint assembly may include a profile ring including a cam profile, a rotor configured to rotate relative to the profile ring, and an elastic body configured to connect to the rotor, and to store an elastic potential energy corresponding to the cam profile in response to the rotor rotating relative to the profile ring.

20 Claims, 23 Drawing Sheets

(51) Int. Cl.
  *A61F 2/70*   (2006.01)
  *A61F 2/72*   (2006.01)
(52) U.S. Cl.
  CPC ............ *A61H 2201/1642* (2013.01); *A61H 2201/5058* (2013.01); *A61H 2201/5069* (2013.01); *A61H 2201/5071* (2013.01); *A61H 2201/5079* (2013.01); *A61H 2201/5084* (2013.01)

(56) References Cited

U.S. PATENT DOCUMENTS

| | | |
|---|---|---|
| 2009/0092442 A1 | 4/2009 | Shim et al. |
| 2015/0182408 A1 | 7/2015 | Roh et al. |
| 2015/0231018 A1 | 8/2015 | Shim et al. |

FOREIGN PATENT DOCUMENTS

| | | |
|---|---|---|
| JP | 2012100983 A | 5/2012 |
| JP | 2013-066669 A | 4/2013 |
| JP | 2015023949 A | 2/2015 |
| KR | 20060039970 A | 5/2006 |
| KR | 2013-0045826 A | 5/2013 |
| WO | WO-14092162 | 6/2014 |

\* cited by examiner

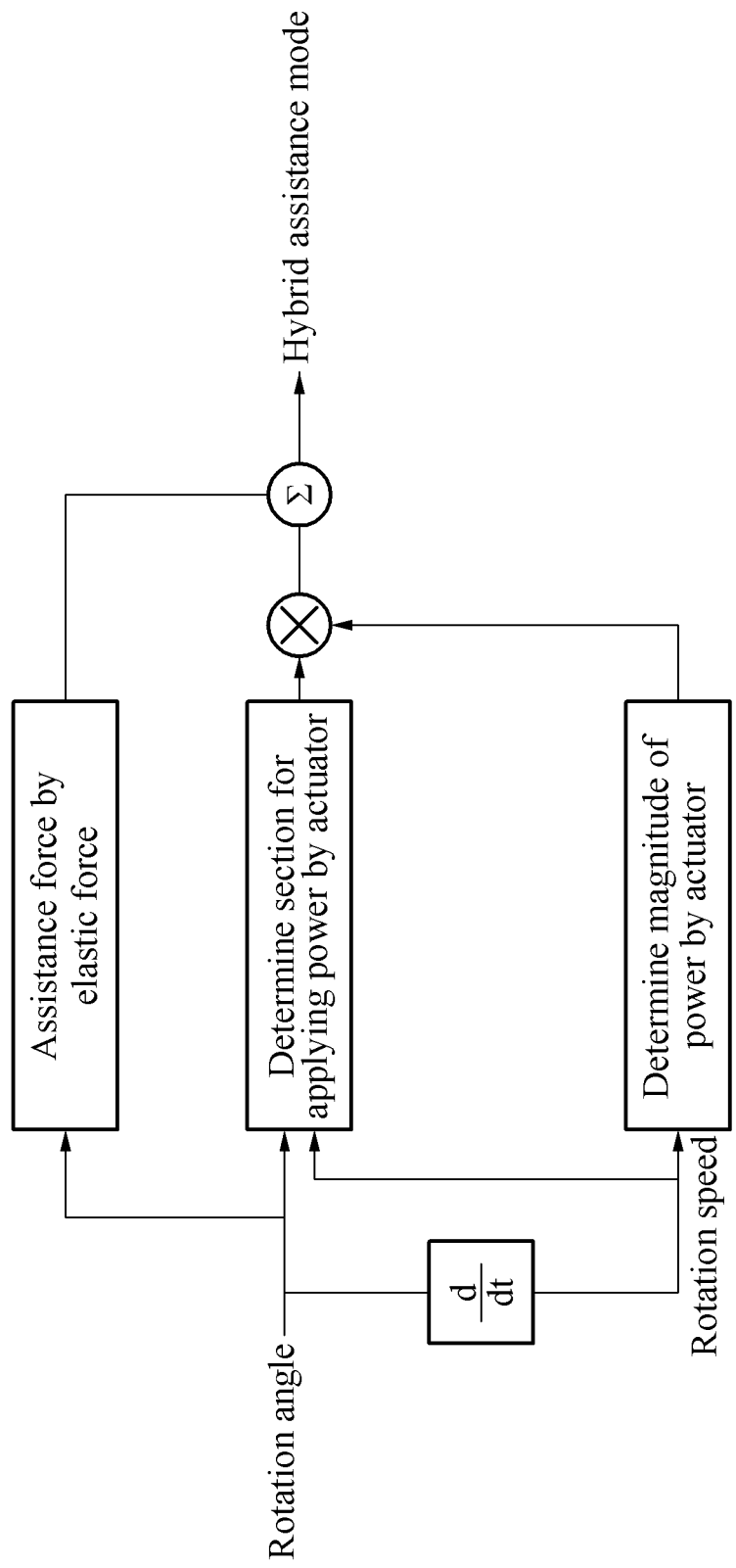

US 10,583,062 B2

JOINT ASSEMBLY AND MOTION ASSISTANCE DEVICE COMPRISING THE JOINT ASSEMBLY

CROSS-REFERENCE TO RELATED APPLICATION

This application claims under 35 U.S.C. § 119 to Korean Patent Application No. 10-2015-0154621, filed on Nov. 4, 2015, in the Korean Intellectual Property Office, the entire contents of which are incorporated herein by reference in its entirety.

BACKGROUND

1. Field

At least one example embodiment relates to a joint assembly and/or a motion assistance device including the joint assembly.

2. Description of the Related Art

A motion assistance device may be utilized for military and commercial purposes and may be applicable to support daily lives and rehabilitations of seniors, musculoskeletal patients, and the disabled.

With the onset of rapidly aging societies, an increasing number of persons may experience pain and/or inconvenience from joint issues. Accordingly, there is increasing interest in motion assistance devices that may assist seniors and/or patients having joint issues with walking.

For increased convenience, a user may desire the motion assistance device to be wearable for a relatively long-time, to allow a limitless motion, to be light and readily portable, and to provide power for a relatively long time on a single charge.

SUMMARY

Some example embodiments relate to a joint assembly.

In some example embodiments, the joint assembly may include a profile ring including a cam profile; a rotor configured to rotate relative to the profile ring; and an elastic body connected to the rotor, the elastic body configured to store an elastic potential energy in response to the rotor rotating relative to the profile ring such that the elastic potential energy corresponds to a shape of the cam profile.

In some example embodiments, the joint assembly may further include a fixed ring enclosing the profile ring therein such that the profile ring selectively rotates relative thereto; and a binder configured to selectively couple the profile ring to one of the rotor and the fixed ring.

In some example embodiments, the rotor is configured to rotate relative to the profile ring such that the elastic potential energy of the elastic body varies, if the binder couples the profile ring to the fixed ring, and the rotor and the profile ring are configured to rotate as a single rigid body such that the elastic potential energy of the elastic body is static, if the binder couples the profile ring to the rotor.

In some example embodiments, the joint assembly may further include a pressurizing portion connected to a first end of the elastic body; and a roller connected to the pressurizing portion, the roller configured to contact the cam profile with an elastic force generated by the elastic body.

In some example embodiments, the elastic body includes a first elastic body and a second elastic body, the first elastic body and the second elastic body connected to a first end and a second end of a first surface of the pressurizing portion, respectively, with a center of rotation of the rotor therebetween.

In some example embodiments, a second end of the elastic body is within a cylinder hole in the rotor, and the joint assembly further includes a friction reduction member between a side surface of the elastic body and an inner surface of the cylinder hole, the friction reducing member configured to reduce friction between the elastic body and the rotor.

In some example embodiments, the rotor is configured to rotate such that a distance from a center of rotation of the rotor to an end of the roller is maximum when the rotor in an initial state.

In some example embodiments, the shape of the cam profile is such that a distance from a center of rotation of the rotor to a portion of the cam profile is less than or equal to a minimum distance from the center of rotation of the rotor to an end of the roller.

In some example embodiments, the shape of the cam profile is such that both sides of the cam profile relative to an initial position of the rotor are asymmetric.

Some other example embodiments relate to a joint assembly.

In some example embodiments, the joint assembly includes a profile ring including a cam profile; a rotor configured to rotate relative to the profile ring; a cable configured to wind around the cam profile in response to rotation of the rotor; and an elastic body connected to the cable, the elastic body configured to store an elastic potential energy in response to winding of the cable.

In some example embodiments, the joint assembly further includes a fixed ring enclosing the profile ring such that the profile ring rotates relative thereto; and a binder configured to selectively couple the profile ring to one of the rotor and the fixed ring.

In some example embodiments, the rotor is configured to rotate relative to the profile ring such that the cable is wound around the cam profile to vary the elastic potential energy of the elastic body, if the binder couples the profile ring to the fixed ring, and the rotor and the profile ring are configured to rotate as a single rigid body such that the elastic potential energy of the elastic body is static, if the binder couples the profile ring to the rotor.

In some example embodiments, the rotor includes a slack prevention slot along a circumference thereof and the profile ring includes a guide slot along a circumference thereof corresponding to the slack prevention slot, and the joint assembly further includes a cable holder connected to one side of the cable, the cable holder configured to move within the guide slot and the slack prevention slot.

In some example embodiments, a length of the guide slot is greater than a length of the slack prevention slot.

In some example embodiments, the elastic body includes a first elastic body and a second elastic body, the cable includes a first cable and a second cable, a first end of the first cable and a first end of the second cable connected to the first elastic body and second elastic body, respectively, the cable holder includes a first cable holder and a second cable holder connected to a second end of the first cable and a second end of the second cable, respectively, and the guide slot includes a first guide slot and a second guide slot configured to direct the first cable holder and the second cable holder, respectively.

In some example embodiments, the rotor includes a rotary body; and an extending body extending from the rotary body, the extending body having a first side and a second side, the first elastic body and the second elastic body on the first and second side of the extending body, respectively.

In some example embodiments, the joint assembly further includes a plurality of idlers adjacent to the extending body, wherein the cable is wound between the extending body and the idlers to adjust a tension in the cable.

In some example embodiments, the joint assembly further includes a stopper on the fixed ring, the stopper configured to resist rotation of one or more of the rotor and the profile ring, if the rotor or the profile ring contacts the stopper.

In some example embodiments, the cam profile is shaped such that both sides of the cam profile relative to an initial position of the rotor are asymmetric.

In some example embodiments, the joint assembly further includes a fixed ring enclosing the profile ring such that the profile ring rotates relative thereto, wherein the elastic body is configured to vary the elastic potential energy when the cable winds around the cam profile.

In some example embodiments, the rotor includes a slack prevention slot along a circumference thereof and the profile ring includes a guide slot along a circumference thereof corresponding to the slack prevention slot, and the joint assembly further includes a cable holder connected to one side of the cable, the cable holder configured to move within the guide slot and the slack prevention slot such that, when the cable holder moves to one end of the guide slot, the rotor is configured to rotate together with the profile ring.

In some example embodiments, the joint assembly further includes a stopper on the fixed ring, the stopper configured to resist rotation of one or more of the rotor and the profile ring such that, when the stopper resists the rotation of the profile ring, the rotor is configured to rotate while the profile ring is stationary to vary a magnitude of the elastic potential energy of the elastic body.

Some example embodiments relate to a motion assistance device.

In some example embodiments, the motion assistance device includes a fixing device configured to attach to a first portion of a body of a user; a support configured to provide an assistance force to a second portion of the body of the user; a driver including an actuator configured to supply power; and a joint assembly connected to the fixing device and the support, the joint assembly configured to transfer the power from the actuator and an additional power provided by an elastic force as the assistance force to the support.

In some example embodiments, the joint assembly includes a fixed ring connected to the fixing device; a rotor connected to the support, the rotor configured to selectively receive the power from the actuator; a profile ring including a cam profile, the profile ring configured to rotate relative to the fixed ring and the rotor; and an elastic body configured to store an elastic potential energy that varies in response to rotation of the rotor.

In some example embodiments, the motion assistance apparatus selectively operates in one of at least four operating modes, the four operating modes including, a passive assistance mode in which the rotor is driven by the elastic potential energy stored in the elastic body; an active assistance mode in which the rotor is driven by the power supplied from the actuator connected to the rotor; a hybrid assistance mode in which the rotor is driven by both the power supplied from the actuator and the elastic potential energy stored in the elastic body; and a free mode in which the rotor is manually driven by a force provided from a user.

In some example embodiments, the joint assembly further includes a binder configured to selectively couple the profile ring to one of the rotor and the fixed ring.

In some example embodiments, the binder is configured to couple the profile ring to the fixed ring and the actuator is configured to not transfer the power to the rotor, if the motion assistance apparatus is operating in the passive assistance mode, the binder is configured to couple the profile ring to the rotor and the actuator is configured to transfer the power to the rotor, if the motion assistance apparatus is operating in the active assistance mode, the binder is configured to couple the profile ring to the fixed ring and the actuator is configured to transfer the power to the rotor, if the motion assistance apparatus is operating in the hybrid assistance mode, and the binder is configured to couple the profile ring to the rotor and the actuator is configured to not transfer the power to the rotor, if the motion assistance apparatus is operating in the free mode.

In some example embodiments, the motion assistance apparatus further includes a controller configured to instruct an actuator to move the binder to one of a first position and a second position, the first position being a position in which the binder couples the profile ring to the rotor and the second position being a position in which the binder couples the profile ring to the fixed ring.

In some example embodiments, the motion assistance apparatus further includes one or more sensors configured to sense information related to a motion of the user, wherein the controller is configured to analyze the information related to the motion of the user, and to transmit an instruction to one or more of the driver and the joint assembly to set an operating mode of the motion assistance device to one of the four operating modes based thereon.

In some example embodiments, the controller is configured to analyze the information to determine whether the user is walking with difficulty, and set the operating mode of the motion assistance device to one of the active assistance mode and the hybrid assistance mode, if the user is walking with difficulty.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 7 is a diagram illustrating an operation process in a hybrid assistance mode according to at least one example embodiment;

DETAILED DESCRIPTION

Figure 1:
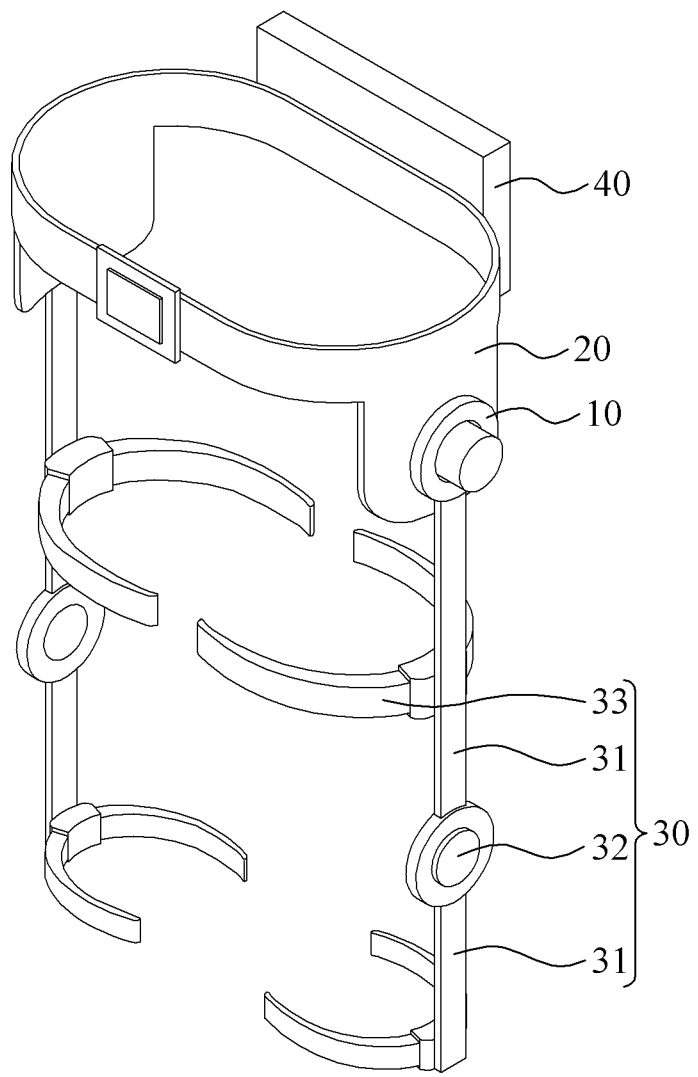
FIG. 1 is a perspective view illustrating a motion assistance device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

FIG. 1 is a perspective view illustrating a motion assistance device according to at least one example embodiment.

Referring to FIG. 1, a motion assistance device 1 may be worn by a user and may assist a motion of the user. The user may be, for example, a human being, an animal, and a robot, however, the example embodiments are not limited thereto.

Further, although FIG. 1 illustrates an example in which the motion assistance device 1 assists a motion of a thigh portion of the user, the motion assistance device 1 may also assist another portion of an upper body, such as a hand, an upper arm, a lower arm, etc., or another portion of a lower body, such as a hip, a knee, a foot, a calf, etc. That is, the motion assistance device 1 may assist a motion of a portion of the user.

Hereinafter, for clarity, a description will be made based on an example in which the motion assistance device 1 assists a lower body of a user, particularly, a motion of a thigh portion of the user.

The motion assistance device 1 may include a joint assembly 10, a fixing module (or, alternatively, a fixing device) 20, a supporting module (or, alternatively, a support) 30 and a driving module (or, alternatively, a driver) 40.

The fixing module 20 may be attached to the user. The fixing module 20 may be in contact with at least a portion of an external body of the user. The fixing module 20 may support the rear of the user and a portion of the fixing module 20 may be provided in a shape to cover the external body of the user along the external body of the user. For example, the fixing module 20 may be fixed to a back of the user and may partially cover a waist of the user.

Although not illustrated, the fixing module 20 may include a length adjustment device configured to adjust a length of the fixing module 20 to fit for the user. For example, the length adjustment device may include a buckle structure, a rack-and-pinion structure, a hook and loop structure, or an elastic body structure.

In the case of employing the rack-and-pinion structure, the fixing module 20 may include a plurality of frames. A rack gear and a pinion gear each in which a frame is formed may slide through mutual engagement, thereby adjusting the length of the fixing module 20.

Alternatively, in the case of employing the hook and loop structure, the length of the fixing module 20 may be adjusted by modifying an attachment position of a hook or loop member. As another example, in the case of employing the elastic body structure, the length of the fixing module 20 may be adjusted since a length of an elastic body extends in correspondence to the periphery of a wearing portion of the user.

The driving module 40 may supply a power to the joint assembly 10, which will be described later, and may include an actuator configured to be supplied with voltage or current and to generate the power.

The driving module 40 may be provided to a portion of the fixing module 20. In this instance, at least a portion of the driving module 40 may be received in a box and thereby be mounted to the fixing module 20.

The driving module 40 may be attached to the fixing module 20 such that the driving module 40 aligns with a proximal part of the user. The proximal part of the user may indicate a center portion of the user, such as a back, a waist, a torso, etc. For example, the fixing module 20 may be configured to cover the waist of the user and the driving module 40 may be attached to the fixing module 20 and thereby be mounted to the proximal part of the user.

The supporting module 30 may support a portion of the user and may support a partial motion of the user.

The supporting module 30 may include a side supporting body 31. The side supporting body 31 may extend along the side of the lower body of the user. A plurality of side supporting bodies 31 may be provided.

For example, the side supporting bodies 31 may be disposed along a thigh and a calf, respectively, and the side supporting bodies 31 may be connected using a connection joint 32. The connection joint 32 may be disposed to be adjacent to a joint portion and the side supporting bodies 31 may perform a motion similar to a human body.

The side supporting body 31 may be connected to the joint assembly 10 and may be supplied with the power from the joint assembly 10 and thereby operate. However, it is only an example and another portion of the supporting module 30 may be driven to assist a motion of the user.

A front supporting body 33 may fix the supporting module 30 to the thigh or the calf. For example, the front supporting body 33 may extend from the side supporting body 31 and cover the thigh or the calf. The front supporting body 33 may operate together with the side supporting body 31.

However, a configuration of the supporting module 30 is not limited thereto. For example, the supporting module 30 may have different structures in which the supporting module 30 is still supplied with the power from the driving module 40 or the joint assembly 10 to assist a motion of the user.

The joint assembly 10 may connect the driving module 40 and the supporting module 30. For example, one side of the joint assembly 10 may be fixed to the fixing module 20 and thereby be connected to the driving module 40. Another side of the joint assembly 10 may be connected to the supporting module 30.

The joint assembly 10 may be provided at a joint portion of the user and may operate in a similar manner to the joint portion. Referring to FIG. 1, the joint assembly 10 is provided to be adjacent to a femoral region of the user, for example, at a hip joint of the user.

The joint assembly 10 may transfer the power to the supporting module 30.

The joint assembly 10 may drive the supporting module 30 using the power supplied from the driving module 40 or using an elastic potential energy occurring in the joint assembly 10.

The joint assembly 10 may transfer both the external power and the elastic potential energy to the supporting module 30, or may selectively transfer one or more of the external power or the elastic potential energy. The joint assembly 10 may also selectively disable transfer of any of the power to the supporting module 30.

To this end, the joint assembly 10 may include a configuration capable of storing the elastic potential energy.

Hereinafter, a structure of the joint assembly 10 and an operation mode of the joint assembly 10 will be described.

Figure 2:
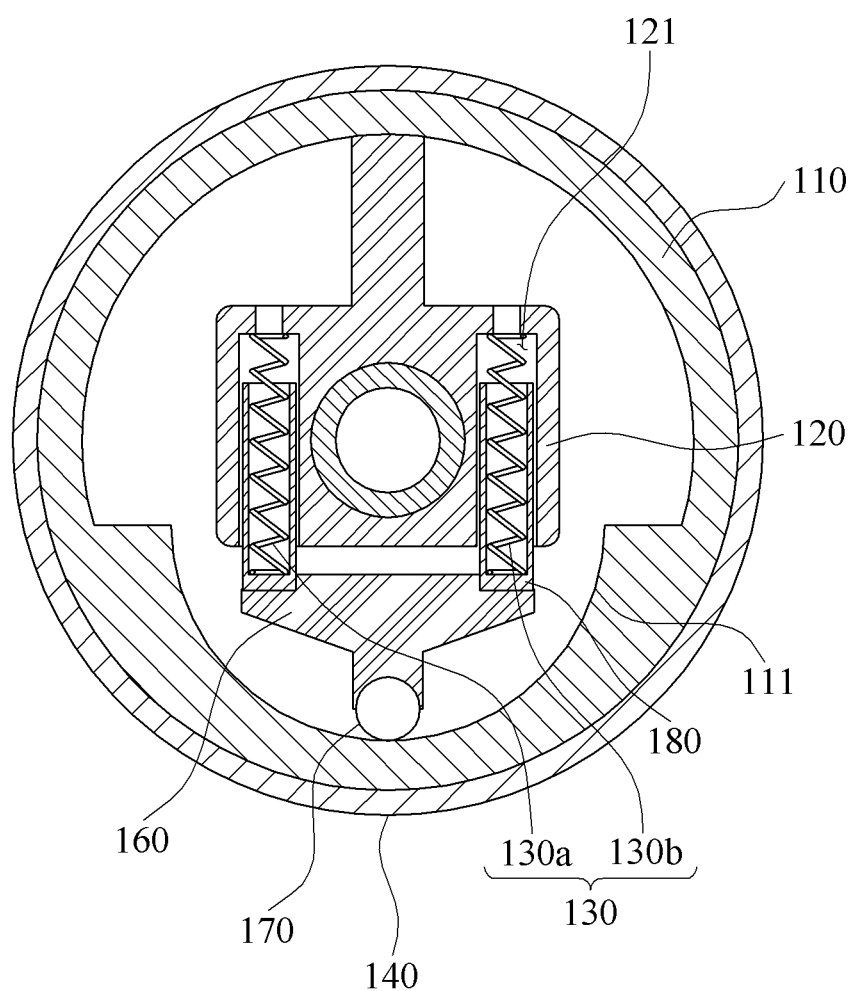
FIG. 2 is a cross-sectional view illustrating an internal structure of a joint assembly according to at least one example embodiment.

FIG. 2 is a cross-sectional view illustrating an internal structure of a joint assembly according to at least one example embodiment.

Referring to FIG. 2, the joint assembly 10 may be configured so that an elastic potential energy of an elastic body 130 may vary in response to rotation of a rotor 120.

The joint assembly 10 may include a profile ring 110 including a cam profile 111 and the rotor 120 configured to rotate relative to the profile ring 110. At least a portion of the rotor 120 may rotate in an internal space of the profile ring 110 formed by the cam profile 111.

The elastic body 130 may be connected to the rotor 120 and, in response to the rotor 120 rotating relative to the profile ring 110, the elastic body 130 may store the elastic potential energy.

For example, the rotor 120 may rotate within the profile ring 110 along the cam profile 111, and with the elastic body 130 connected to the rotor 120 being pressed, the elastic potential energy corresponding to the cam profile 111 may be stored in the elastic body 130.

To this end, the rotor 120 and one side of a pressurizing portion 160 may be connected to the elastic body 130, and a roller 170 may be disposed on another side of the pressurizing portion 160. Due to an elastic force of the elastic body 130, the roller 170 may maintain a contact state with the cam profile 111.

The rotor 120 may be driven by a motion of the user or the external power. For example, the rotor 120 may be connected to the driving module 40 and the supporting module 30.

When the rotor 120 rotates in the profile ring 110, the pressurizing portion 160 may move along the cam profile 111 by way of the roller 170 such that the elastic body 130 may be pressed or extended.

The elastic body 130 may include a first elastic body 130a and a second elastic body 130b, and the first elastic body 130a and the second elastic body 130b may be connected to first and second sides of the pressurizing portion 160, respectively.

Due to the above structure, a position of the pressurizing portion 160 may be stably maintained. The elastic potential energy may be efficiently stored in the elastic body 130 regardless of a rotation direction of the elastic body 130.

A portion of the elastic body 130 may be within the rotor 120 and another portion of the elastic body 130 may be exposed outside the rotor 120. For example, a number of cylinder holes 121 corresponding to the number of elastic bodies 130 may be formed in the rotor 120, and a portion of each of the elastic body 130 may be accommodated in a respective one of the cylinder holes 121.

The elastic body 130 may be pressed or extended within the cylinder hole 120, and a friction reduction member 180 may reduce a friction occurring between the elastic body 130 and an inner surface of the cylinder hole 121. For example, the friction reduction member 180 may include a linear bushing.

The friction reduction member 180 may be disposed between the elastic body 130 and the inner surface of the cylinder hole 121, and may be configured to surround the elastic body 130.

The friction reduction member 180 may be formed based on a compression level of the elastic body 130. For example, when the rotor 120 does not rotate, that is, is in a stationary state, the rotor 120 and the pressurizing portion 160 may be disposed to be separate from each other by way of the elastic body 130. Therefore, when the rotor 120 is in the stationary state, the friction reduction member 180 may be configured to be in contact with the pressurizing portion 160 and to be separate from an end of the cylinder hole 121.

When the elastic body 130 is pressed and in response thereto, the rotor 120 and the pressurizing portion 160 contact with each other, the friction reduction member 180 may be in contact with the end of the cylinder hole 121. That is, the friction reduction member 180 may be formed to correspond to a maximally pressed length of the elastic body 130.

Due to the above structure, the friction reduction member 180 may reduce the friction between the elastic body 130 and the inner surface of the cylinder hole 121 without obstructing the elastic body 130 that is being pressed.

As another example, a length of the friction reduction member 180 may be configured to vary in response to compression or extension of the elastic body 130 by employing a sliding structure.

The cam profile 111 may indicate a shape of the inner surface of the profile ring 110. In response to the roller 170 moving along the cam profile 111, the elastic body 130 may be pressed and may store the elastic potential energy corresponding to the cam profile 111. The cam profile 111 will be further described below.

The joint assembly 10 may include a fixed ring 140. For example, the fixed ring 140 may be fixed to the fixing module 20 to fix a position of the joint assembly 10. The profile ring 110 may rotate relative to the fixed ring 140.

The fixed ring 140 may selectively couple with the profile ring 110, which will be described below. When the fixed ring 140 selectively couples with the profile ring 110, the rotor 120 alone may rotate relative to the profile ring 110.

Alternatively, the profile ring 110 may selectively couple with the rotor 120. When the profile ring 110 selectively couples with the rotor 120, the profile ring 110 and the rotor 120 may perform a rigid body motion in relation to the fixed ring 140.

A coupling relationship of the fixed ring 140, the profile ring 110, and the rotor 120 will be further described below.

Figure 3A:
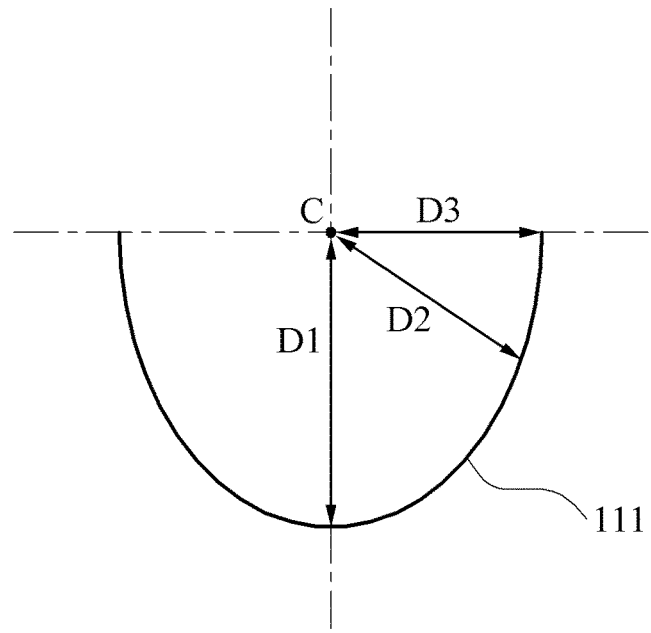
FIGS. 3A and 3B illustrate examples of a cam profile according to at least one example embodiment.
Figure 3B:
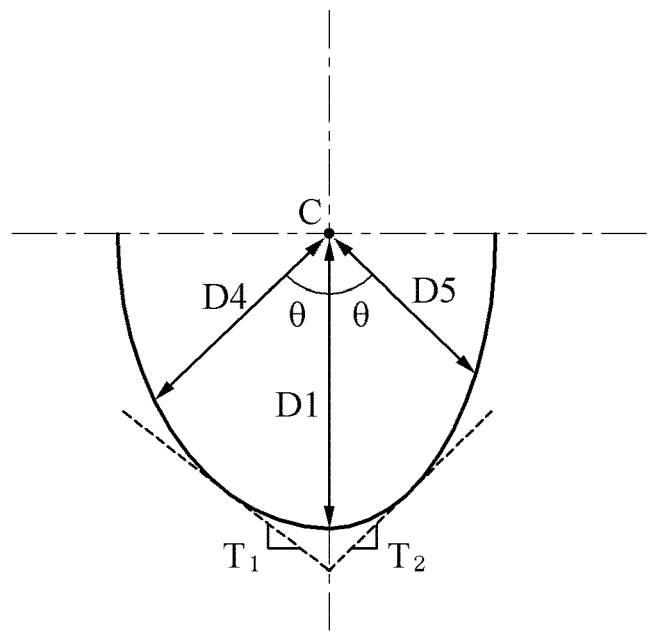

FIGS. 3A and 3B illustrate examples of a cam profile according to at least one example embodiment. FIG. 3A illustrates a form in which the cam profile has a gradually reducing diameter, and FIG. 3B illustrates a form in which the cam profile is asymmetric.

Referring to FIGS. 3A and 3B, the shape of the cam profile 111 may be determined based on a rotation angle of the rotor 120, torque according thereto, a distance from the center of rotation of the rotor 120 to the roller 170, and the like.

For example, the shape of the cam profile 111 may be determined based on a centrifugal force according to a rotation angle of the rotor 120, a reaction force by a contact between the rotor 120 and the cam profile 111, and an elastic force by the elastic body 130. The shape of the cam profile 111 may be determined depending on whether the rotor 120 operates within a set movable range and whether the rotor 120 provides a sufficient assistance force.

The shape of the cam profile 111 may be designed based on the user, a use purpose, and the like, for example the shape may be designed based on the desired amount of elastic potential energy provided by the joint assembly 10.

Hereinafter, although the shape of the cam profile 111 will be described using an example, the shape of the cam profile 111 is not limited thereto and may be designed differently by considering the above matters.

Referring to FIG. 3A, the cam profile 111 may be formed so that a diameter of one side is greater than a diameter of another side.

In an example in which a state in which the rotor 120 does not rotate is an initiate state and a distance from the center of rotation C of the rotor 120 to the cam profile 111 is a center distance D1, the center distance D1 may be configured to be greater than or equal to a distance D2 and/or D3 from the center of rotation C of the rotor 120 having rotated to the end of the roller 170.

That is, a distance from the center of rotation C of the rotor 120 to the end of the roller 170 may be configured to be maximized in the initial state.

Since the distance from the center of rotation C of the rotor 120 to the end of the roller 170 is greatest in the initial state, the elastic body 130 may be pressed in response to rotation of the rotor 120 and accordingly, the elastic potential energy may be stored in the elastic body 130.

Among distances from the center of rotation C of the rotor 120 to the end of the roller 170, the distance D3 may be less than the distance D2 in a state in which the rotor 120 and the pressurizing portion 160 are in contact due to contraction of the elastic body 130.

That is, a portion of diameters of the cam profile 111 may be formed to be less than a minimum distance from the center of rotation C to the end of the roller 170, thereby preventing the rotor 120 from rotating beyond a preset angle or more. The above configuration may prevent the rotor 120 from malfunctioning beyond the normal operation range.

Referring to FIG. 3B, both sides of the cam profile 111 may be asymmetric based on an initial position.

As described above, since the elastic body 130 stores the elastic potential energy according to the cam profile 111, the cam profile 111 may be determined based on the power required for a rotation direction of the rotor 120. Accordingly, a magnitude of the elastic potential energy to be stored may vary based on the rotation direction of the rotor 120.

For example, when the joint assembly 10 is applied to the motion assistance device 1 assisting a lower body motion of the user, the power required for each walking stage of the user may be different.

In this example, when a leg of the user to which the joint assembly 10 is provided moves forward and is in contact with a floor, the rotor 120 may rotate toward one side of an inner ring and a motion for rotating a body of the user may be initiated based on a contact point between the leg and the floor.

Here, the leg of the user to which the joint assembly 10 is provided may generate a rotary power in a state in which the leg of the user is spread. At the same time, an opposite leg of the user may be bent and move toward the rear of the body.

When the body of the user moves forward, the opposite leg of the user may also move forward and may become in contact with the floor. At the same time, the leg of the user to which the joint assembly 10 is provided may move forward the rear of the body in a bent state.

During this process, the rotor 120 may rotate toward another side of the inner ring and the elastic potential energy may increase, thereby decelerating a motion of the leg of the user.

When the leg of the user rotates based on the initial position, the elastic potential energy may be stored. When the leg of the user moves toward the initial position, the elastic potential energy may provide an assistance force.

Here, a relatively great assistance force may be required when the leg of the user is positioned at the rear of the body of the user compared to a case in which the leg of the user is positioned ahead of the body of the user. Alternatively, when the leg of the user is positioned at the rear of the body of the user, a rotation angle is relatively great and thus, a relatively great elastic potential energy may be stored compared to a case in which the leg of the user is positioned ahead of the body of the user.

By forming both sides of the cam profile 111 to be asymmetric into consideration of the above feature, the elastic potential energy may be determined to be different based on the rotation direction of the rotor 120.

For example, referring to FIG. 3B, a tilt $T_1$ of one side of the cam profile 111 measured based on an axis that includes the center of rotation C of the rotor 120 may be formed to be less than a tilt $T_2$ of another side of the cam profile 111.

Accordingly, a distance D4 from the center of rotation C to the end of the roller 170 at a position at which the rotor 120 has rotated toward one side at a preset angle may be greater than a distance D5 from the center of rotation C to the end of the roller 170 at a position at which the rotor 120 has rotated toward the other side at a preset angle.

Dissimilar to the examples of FIGS. 3A and 3B, a diameter of the cam profile 111 may be equal to the center distance D1 at a position at which the rotor 120 has rotated toward both sides of the center distance D1 at a preset angle. In this configuration, although the rotor 120 rotates at a preset angle at an initial position, the elastic potential energy of the elastic body 130 may not vary. Accordingly, in a section in which a free motion is required or an assistance force is not required, the user may move without using the elastic force.

As another example, a different assistance force may be provided for each walking stage or both sides of the cam profile 111 may be configured to have different lengths by bending the cam profile 111.

Figure 4:
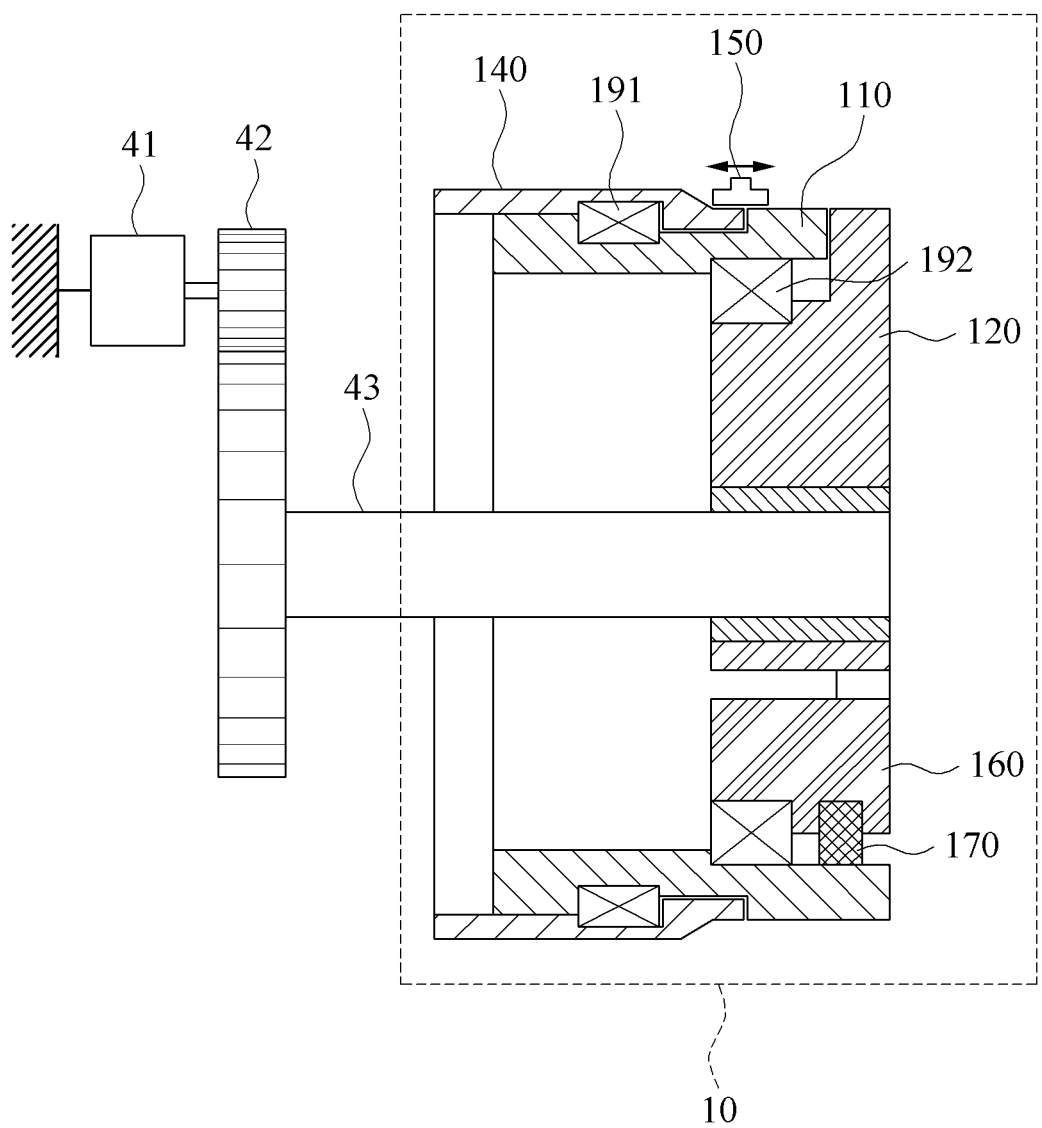
FIG. 4 is a side cross-sectional view illustrating a joint assembly according to at least one example embodiment.

FIG. 4 is a side cross-sectional view illustrating a joint assembly according to at least one example embodiment.

As described above, the rotor 120 may be driven with the power supplied from an outside. For example, a rotational shaft 43 may be connected at the center of the rotor 120 and the rotational shaft 43 may be connected to the driving module 40 to transfer the power to the rotor 120.

Alternatively, the rotational shaft 43 may be connected to a driving gear 42 and the driving gear 42 may be connected to an actuator 41. In this manner, the power may be transferred from actuator 41 to the rotor 120.

The power may be selectively supplied to the rotor 120. That is, the rotor 120 may be driven with the power supplied from an outside, or may rotate only with a motion of the user, instead of using the external power.

The rotor 120 may rotate relative to the profile ring 110, and the profile ring 110 may rotate relative to the fixed ring 140. To assist rotation of the rotor 120 and the profile ring 110, a bearing 191 may be provided between the profile ring 110 and the fixed ring 140 and a bearing 192 may be provided between the profile ring 110 and the rotor 120.

A binder 150 may selectively fix the profile ring 110 to one of the rotor 120 and the fixed ring 140. For example, a stopping step may be formed on the rotor 120, the profile ring 110, and the fixed ring 140. The binder 150 may couple with a stopping step formed between the profile ring 110 and the rotor 120, or a stopping step formed between the profile ring 110 and the fixed ring 140. Here, a coupling method using the binder 150 is not limited thereto and a variety of methods may be used.

When the binder 150 fixes the profile ring 110 to the fixed ring 140, the joint assembly 10 may operate in the aforementioned manner. That is, in response to rotation of the rotor 120, the elastic potential energy may be stored in the elastic body 130, thereby supplying the assistance force to the outside.

When the binder 150 fixes the profile ring 110 to the rotor 120, the rotor 120 may move together with the profile ring 110, instead of moving along the cam profile 111. Accordingly, although the rotor 120 rotates, the elastic potential energy of the elastic body 130 may not vary. Accordingly, the assistance force by the elastic force may not be supplied to the outside.

Due to the above configuration, the user may be selectively supplied with the assistance force by the elastic force. Alternatively, the binder 150 may be automatically controlled and the assistance force by the elastic force may be supplied if an additional assistance force is required. For example, a second actuator (not shown) may be connected to the binder 150 to switch the binder 150 between a first position in which the binder 150 couples the profile ring 110 to the rotor 120 and a second position in which the binder 150 couples the profile ring 110 to the fixing ring 140.

Figure 5:
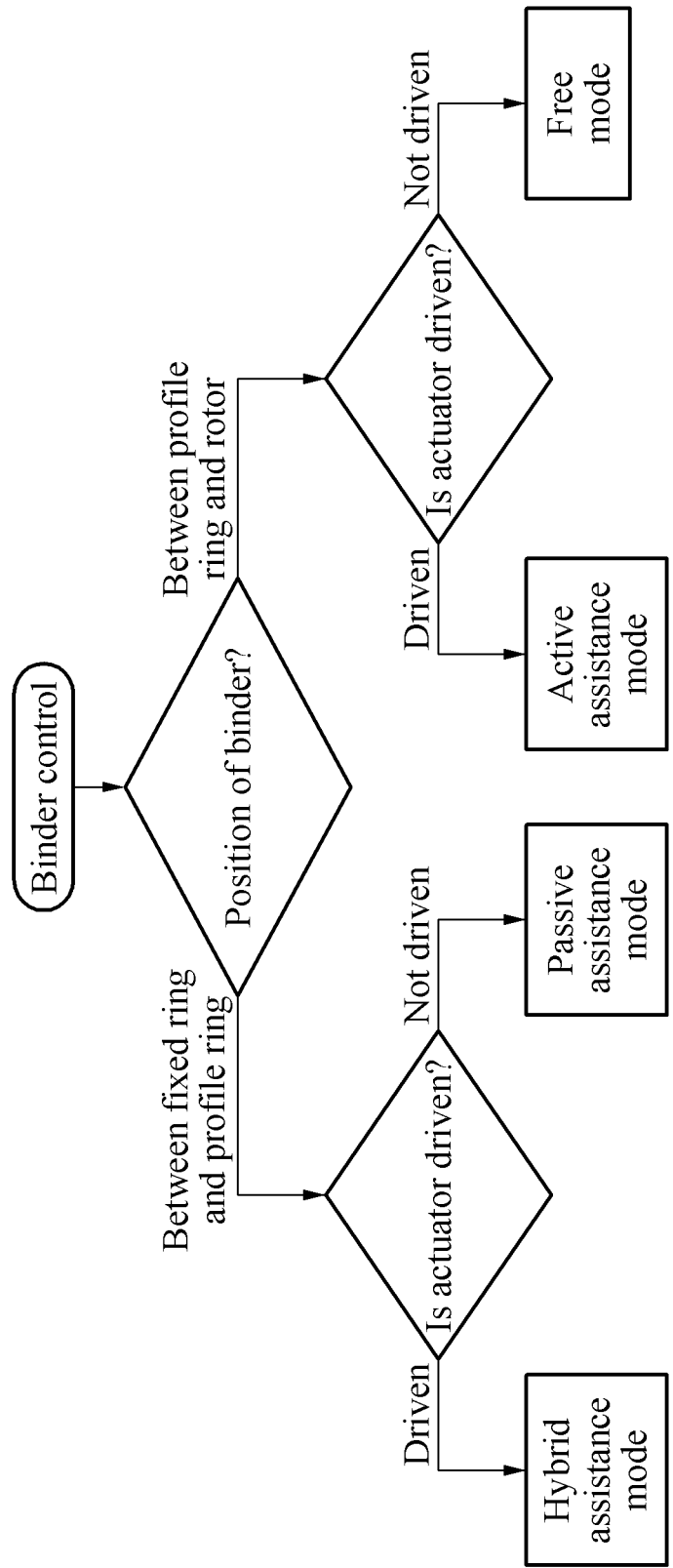
FIG. 5 is a diagram illustrating a process of determining an operation mode of a motion assistance device according to at least one example embodiment.

FIG. 5 is a diagram illustrating a process of determining an operation mode of a motion assistance device according to at least one example embodiment, and FIGS. 6A, 6B, 6C, and 6D are cross-sectional views to describe an operation form of a joint assembly in an operation mode of a motion assistance device according to at least one example embodiment.

Referring to FIGS. 5 and 6A to 6D, an operation mode may be determined based on a control of the binder 150 and a presence/absence of external power.

When the binder 150 is disposed between the fixed ring 140 and the profile ring 110 to couple the profile ring 110 with the fixed ring 140, the assistance force by the elastic force may be supplied.

Figure 6A:
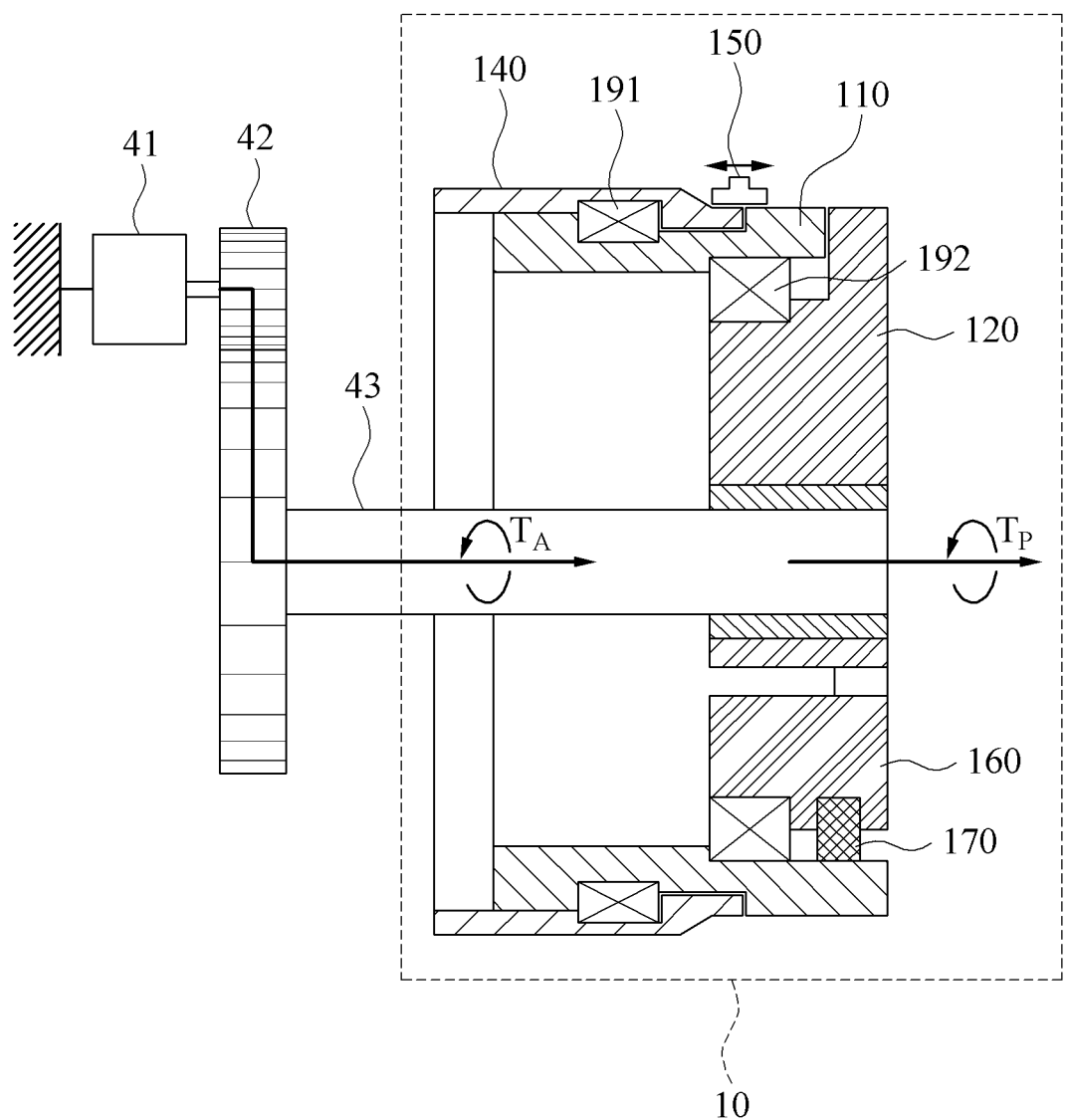
FIGS. 6A, 6B, 6C, and 6D are cross-sectional views to describe an operation form of a joint assembly in an operation mode of a motion assistance device according to at least one example embodiment.

Here, when the power is supplied from the actuator 41, the motion assistance device 1 may operate in a hybrid assistance mode in which all of an assistance force $T_p$ by the elastic force and a power $T_a$ by the actuator 41 are used. FIG. 6A illustrates the joint assembly 10 that operates in the hybrid assistance mode.

Figure 6B:
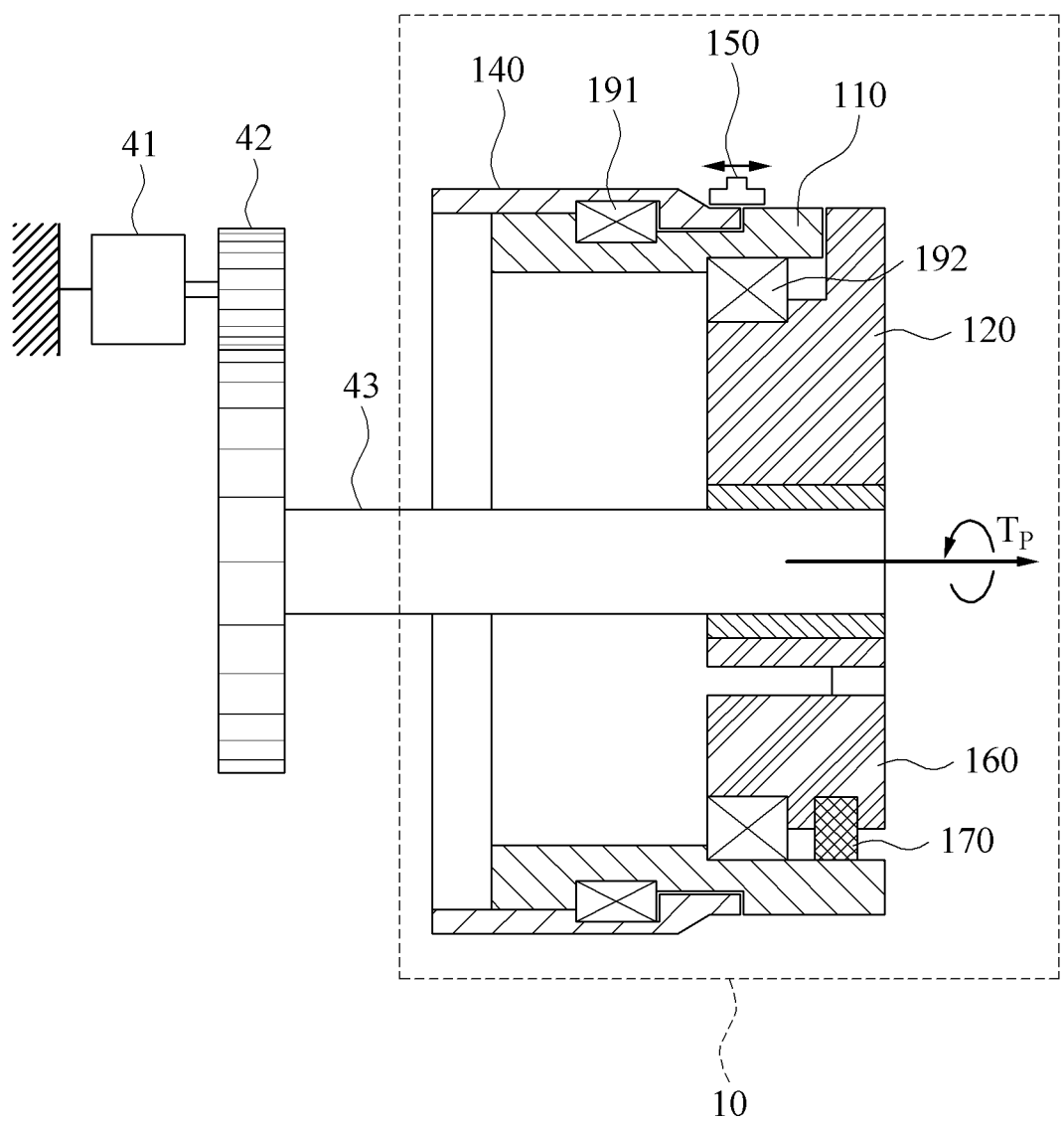

When the power is not supplied from the actuator 41, the motion assistance device 1 may operate in a passive assistance mode in which only the assistance force $T_p$ by the elastic force is supplied. FIG. 6B illustrates the joint assembly 10 that operates in the passive assistance mode.

When the binder 150 is disposed between the profile ring 110 and the rotor 120 to couple the profile ring 110 with the fixed ring 140, the assistance force $T_p$ by the elastic force may not be supplied.

Figure 6C:
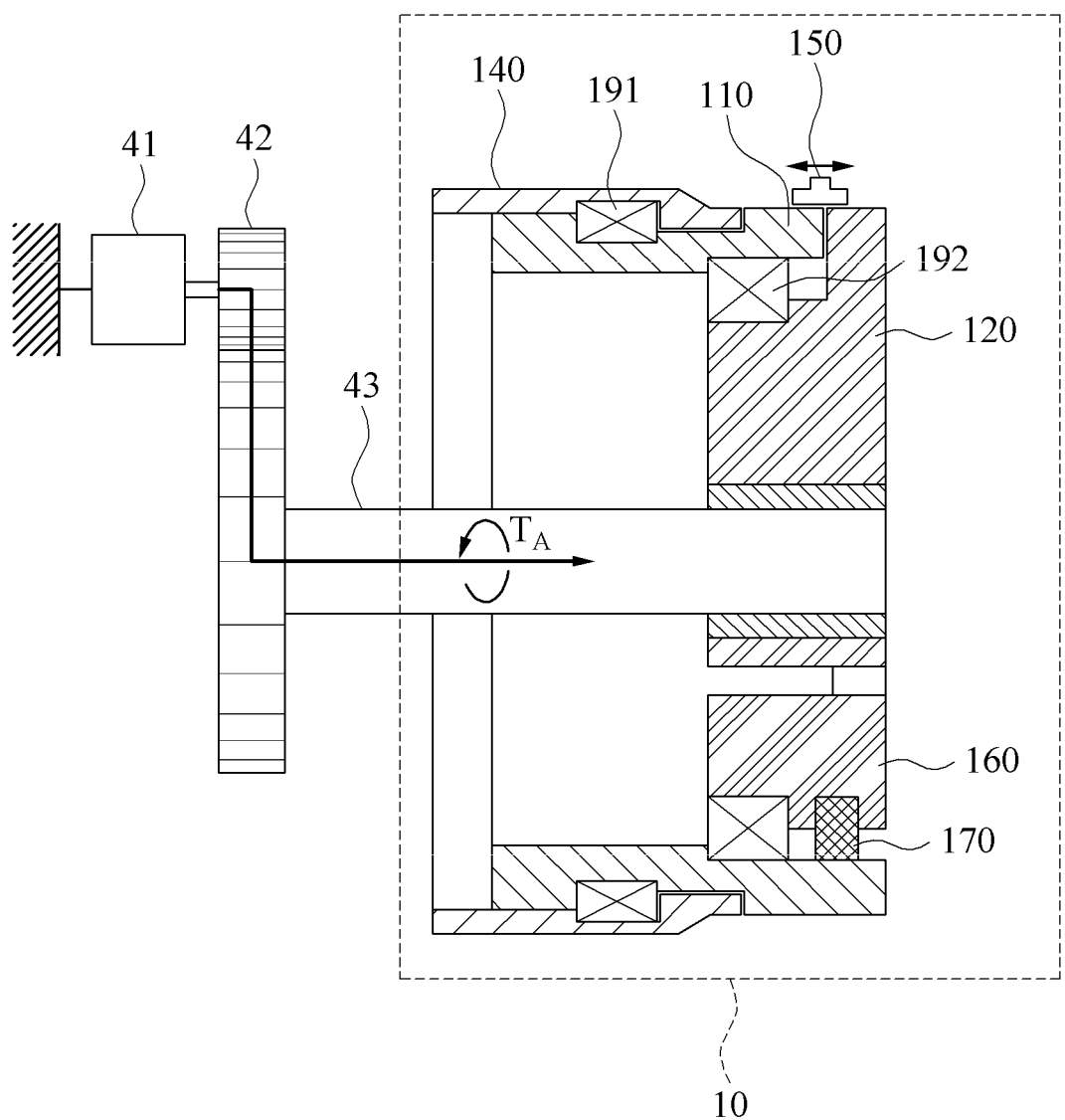

When the power is supplied from the actuator 41, the motion assistance device 1 may operate in an active assistance mode in which only the power $T_a$ by the actuator 41 is supplied. FIG. 6C illustrates the joint assembly 10 that operates in the active assistance mode.

Figure 6D:
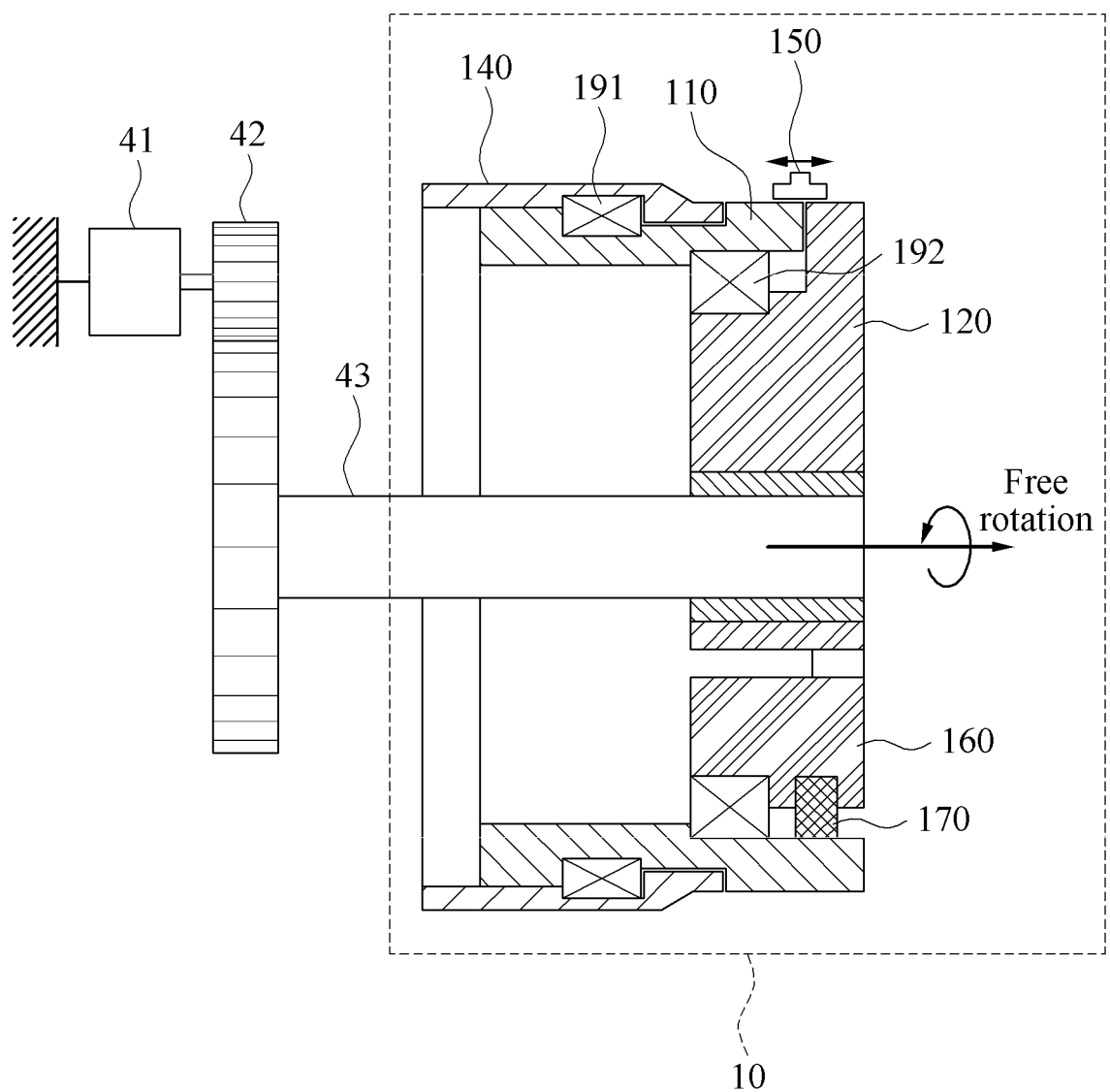

When the power is not supplied from the actuator 41, the motion assistance device 1 may operate in a free mode in which the motion assistance device 1 operates only using a motion of the user. FIG. 6D illustrates the joint assembly 10 that operates in the free mode.

FIG. 7 is a diagram illustrating an operation process in a hybrid assistance mode according to at least one example embodiment.

Referring to FIG. 7, the hybrid assistance mode may be a mode in which all of a power by the actuator 41 and an assistance force by an elastic force are used.

For example, when the motion assistance device 1 assists a walking of the user, the joint assembly 10 provided at a joint portion of the user may operate along a motion of the joint portion.

In the hybrid assistance mode, the assistance force provided by the elastic force and the power provided by the actuator 41 may be determined based on a rotation angle or a rotation speed of the rotor 120.

Initially, an operation section of the assistance force by the elastic force and the power by the actuator 41 may be determined based on the rotation angle.

Since the elastic force is used in the hybrid assistance mode, an elastic potential energy may be stored while the rotor 120 rotates along walking of the user. The elastic potential energy may be determined based on the rotation angle, and a magnitude of the elastic potential energy may vary based on a type of the elastic body 130 and a shape of the profile ring 110.

The power by the actuator 41 may be supplied in a section of a walking assistance profile in which a relatively great assistance force is required. For example, a portion of a gait cycle where the user is performing a large amount of positive work.

For example, based on an initial position of the rotor 120, the power by the actuator 41 may not work in a relatively small rotation angle section and may work in response to an increase in the rotation angle.

Alternatively, the elastic potential energy may increase according to an increase in the rotation angle and, therefore, since a relatively great force may be required for the rotation by the elastic force, the actuator 41 may provide power to assist a motion of the user.

Subsequently, a magnitude of the power by the actuator 41 may be determined based on the rotation speed. A different power level may be required when the user walks slowly and when the user walks fast. Accordingly, the magnitude of the power by the actuator 41 may be controlled based on walking speed of the user.

In addition, an operation section of the force by the actuator 41 may be determined based on the rotation speed. For example, the power by the actuator 41 may work in a relatively wide section when the user walks fast rather than when the user walks slowly.

The magnitude and speed of the power by the actuator 41 in the hybrid assistance mode may be determined based on the aforementioned factors. The power by the actuator 41 and the power by the elastic body 130 may work together whereby the joint assembly 10 may drive the supporting module 30.

FIGS. 8A, 8B, 8C, and 8D are top views illustrating a joint assembly according to at least one example embodiment.

Figure 8A:
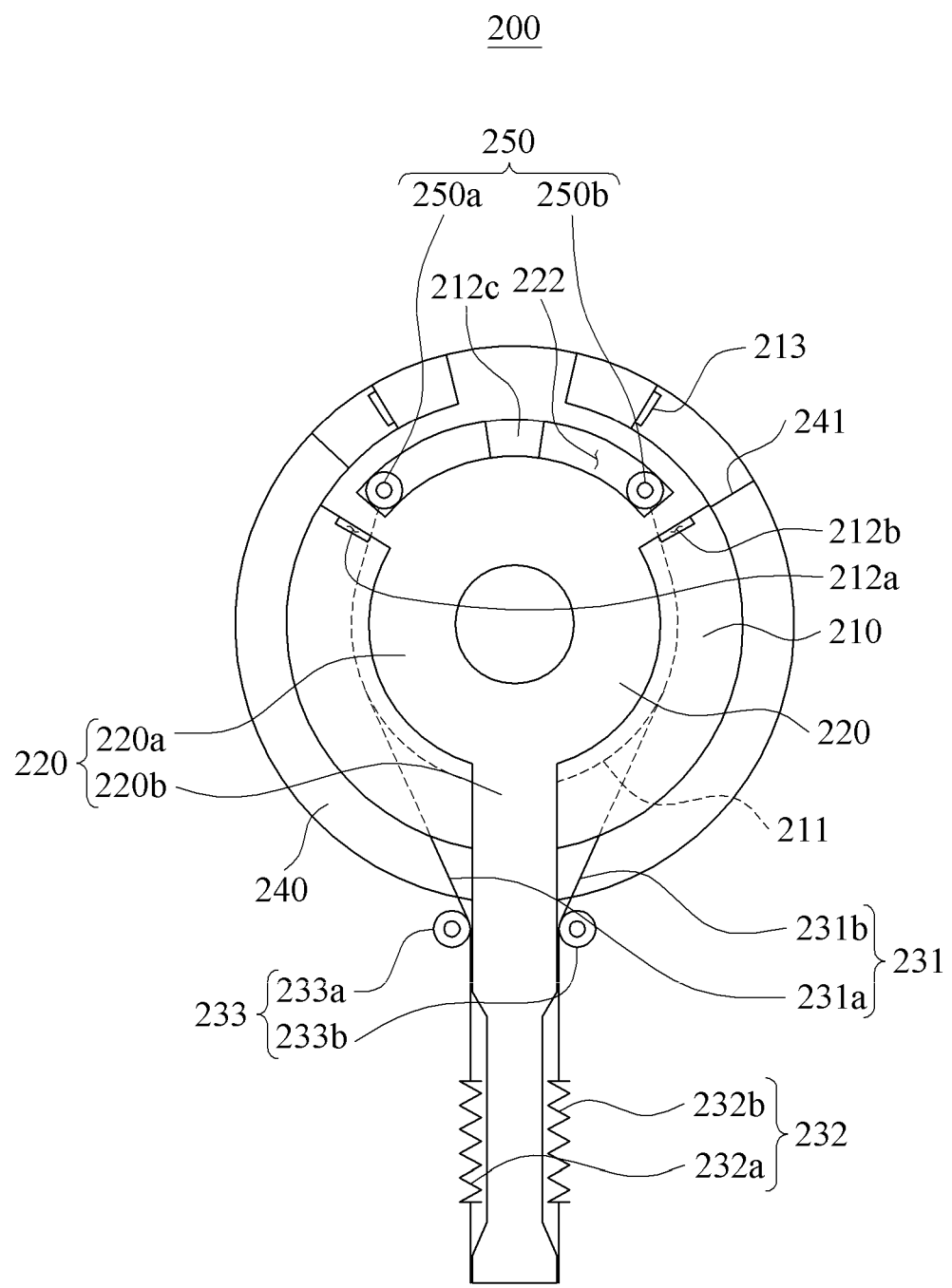
FIGS. 8A, 8B, 8C, and 8D are top views illustrating a joint assembly according to at least one example embodiment.
Figure 8B:
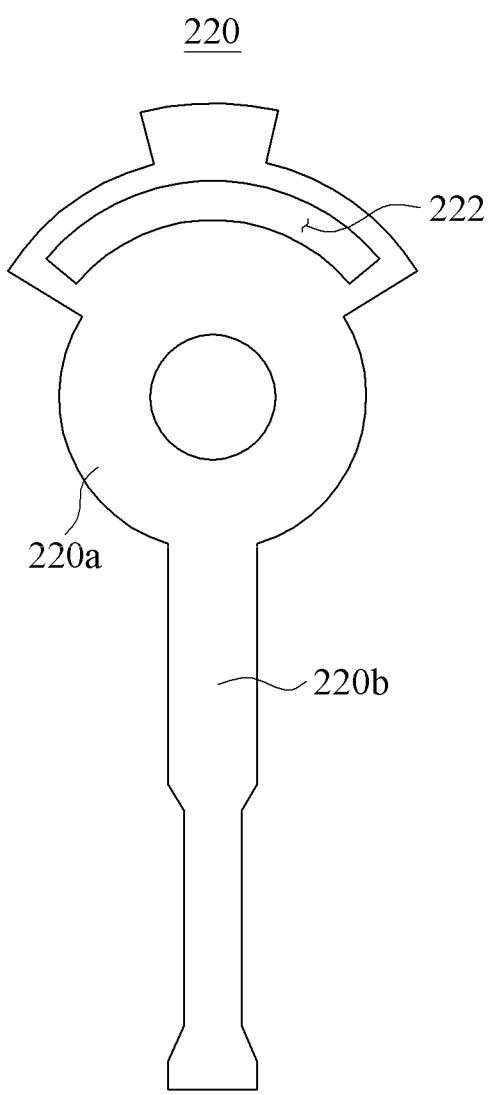
Figure 8C:
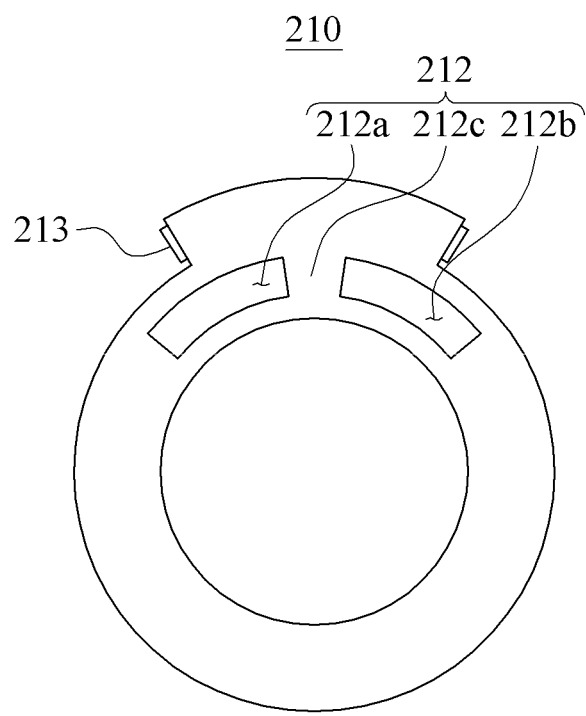
Figure 8D:
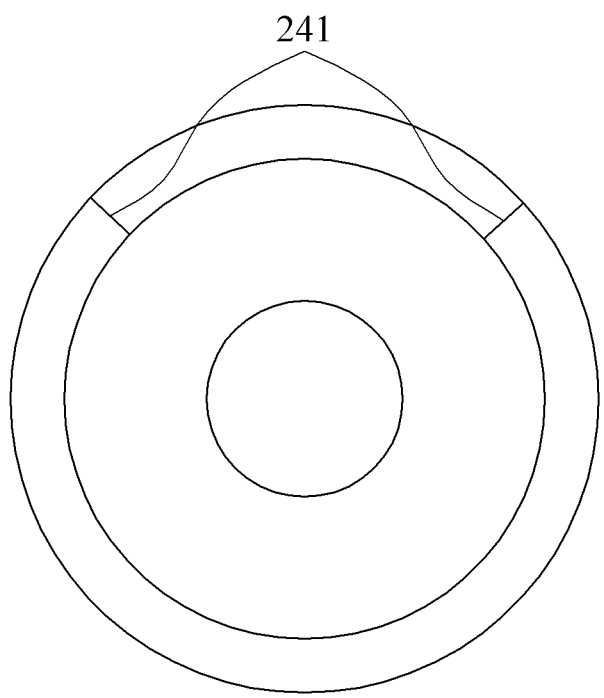

FIG. 8A illustrates a coupling state of the joint assembly, FIG. 8B illustrates a shape of an internal rotor, FIG. 8C illustrates a shape of a profile ring, and FIG. 8D illustrates a shape of a fixed ring.

Like names refer to like constituent elements included in the aforementioned example embodiments and constituent elements having common functions. Unless described otherwise, the description made above with the example embodiments may be applicable to the following example embodiments and a further description related thereto will be omitted here.

Referring to FIGS. 8A to 8D, a joint assembly 200 may be configured so that, in response to rotation of a rotor 220 relative to a profile ring 210, a cable 231 is wound around a cam profile 211 and an elastic potential energy of an elastic body 232 varies in response to winding of the cable 231.

The rotor 220 may include a rotary body 220a and an extending body 220b that extends from one side of the rotary body 220a.

Although not illustrated, the rotary body 220a may be connected to the driving module 40 and the extending body 220b may be connected to the supporting module 30. The rotary body 220a may be connected to the actuator 41 by way of the rotational shaft 43 and the driving gear 42 and may be selectively supplied with an external power.

The rotor 220 may rotate relative to the profile ring 210.

A slack prevention slot 222 may be formed on the rotor 220 and a guide slot 212 may be formed on the profile ring 210. The slack prevention slot 222 may be formed along a circumferential direction of the rotor 220 and the guide slot 212 may be formed along a circumferential direction of the profile ring 210. The guide slot 212 may include a first guide slot 212a and a second guide slot 212b.

The slack prevention slot 222 and the guide slot 212 may be formed at corresponding positions. For example, in a state in which the center of the rotary body 220a and the center of the profile ring 210 are matched, the slack prevention slot 222 and the guide slot 212 may be formed to partially overlap.

A length of the guide slot 212 may be greater than a length of the slack prevention slot 222. In an initial state, the guide slot 212 may be configured to extend from both sides of the slack prevention slot 222.

The joint assembly 200 may include the cable 231 and the elastic body 232. The cable 231 may be wound around the cam profile 211 in response to rotation of the rotor 220 and may press or extend the elastic body 232 connected to the cable 231, thereby changing the elastic potential energy of the elastic body 232.

One side of the cable 231 may be connected to one side of the extending body 220b, and another side of the cable 231 may be connected to a cable holder 250. The cable holder 250 may be disposed to pass through the slack prevention slot 222 and the guide slot 212.

An idler 233 for adjusting a tension of the cable 231 may be disposed on one side of the extending body 220b. The idler 233 may be a rotation pulley. The cable 231 may be disposed between the extending body 220b and the idler 233.

Since a position of the idler 233 is variable, the tension of the cable 231 may increase by moving the idler 233 toward the extending body 220b and the tension of the cable 231 may decrease by moving the idler 233 to be away from the extending body 220b.

The elastic body 232 may be provided on both sides of the rotor 220 so that the elastic body 232 may store the elastic potential energy regardless of a rotation direction of the rotor 220.

For example, the elastic body 232 may include a first elastic body 232a and a second elastic body 232b. The first elastic body 232a and the second elastic body 232b may be disposed on both sides of the extending body 220b, respectively.

The cable 231 may include a first cable 231a that is connected to the first elastic body 232a and a second cable 231b that is connected to the second elastic body 232b. Also, the cable holder 250 may include a first cable holder 250a that is connected to the first cable 231a and a second cable holder 250b that is connected to the second cable 231b. In addition, the idler 233 may include a first idler 233a and a second idler 233b. The first idler 233a and the second idler 233b may be disposed on both sides of the extending body 220b, respectively.

The first cable holder 250a and the second cable holder 250b may be disposed to be in contact with both ends of the slack prevention slot 222, respectively. The first cable holder 250a and the second cable holder 250b may be connected to the elastic body 232, thereby maintaining a position of the cable holder 250.

A length of the guide slot 212 may be greater than a length of the slack prevention slot 222. Thus, although the first cable holder 250a and the second cable holder 250b are positioned at both ends of the slack prevention slot 222, respectively, the first cable 250a and the second cable holder 250b may be separate from both ends of the guide slot 212, respectively.

Through the above configuration, it is possible to prevent the cable 231 and the elastic body 232 from becoming slack.

For example, although the second elastic body 232b is extended in response to clockwise rotation of the rotor 220, the first cable holder 250a may be positioned at one end of the slack prevention slot 222 and thus, a minimum distance from the first cable holder 250a to one side of the extending body 220b may be maintained. Accordingly, it is possible to prevent the first cable 231a and the first elastic body 232a from becoming slack.

As illustrated in FIG. 8C, the first guide slot 212a and the second guide slot 212b may be separate from each other by a separator 212c. The first cable holder 250a and the second cable holder 250b may be provided to the first guide slot 212a and the second guide slot 212b, respectively.

A length of the guide slot 212 may indicate a length that includes the first guide slot 212a, the second guide slot 212b, and the separator 212c.

Since the guide slot 212, the cable holder 250, and the slack prevention slot 222 interact with one another due to rotation of the rotor 220, the rotation of the rotor 220 may be limited. For example, the first guide slot 212a and the second guide slot 212b may be formed to have different lengths such that a rotation angle may be limited to be different based on a rotation direction of the rotor 220. A description related thereto will be made below.

The cam profile 211 may be formed on one side of the profile ring 210. In an example in which the rotor 220 is formed on the front surface of the profile ring 210, the cam profile 211 may be formed on the rear surface of the profile ring 210. Alternatively, the profile ring 210 may include a plurality of surfaces and the cam profile 211 may be disposed between the plurality of surfaces.

With the cable 231 being wound around the cam profile 211, the elastic potential energy of the elastic body 232 may vary. That is, the elastic potential energy may be determined based on a shape of the cam profile 211. Similar to the cam profile 111 described with reference to FIGS. 3A and 3B, the cam profile 211 may be asymmetric or may include a curve.

A fixed ring 240 may be fixed to the fixing module 20, thereby fixing a position of the joint assembly 200. The profile ring 210 may rotate relative to the fixed ring 240.

The fixed ring 240 may include a stopper 241 configured to interfere with rotation of the profile ring 210 or the rotor 220. When the rotation of the profile ring 210 or the rotor 220 reaches a preset (or, alternatively, a desired) angle, the rotation of the profile ring 210 or the rotor 220 may be limited by the stopper 241.

For example, the stopper 241 may protrude from the fixed ring 240 and at least a portion of the profile ring 210 and the rotor 220 may be externally protruded, so that the profile ring 210 and the rotor 220 may interfere with the stopper 241.

An impact absorbing member 213 may be formed on the surface on which the profile ring 210 or the rotor 220 interferes with the stopper 241. The impact absorbing member 213 may include a sponge like material, for example, a rubber material.

The impact absorbing material 213 may prevent the profile ring 210 or the rotor 220 from being damaged due to a contact with the stopper 241. FIG. 8C illustrates an example in which the impact absorbing member 213 is formed on the profile ring 210.

Figure 9:
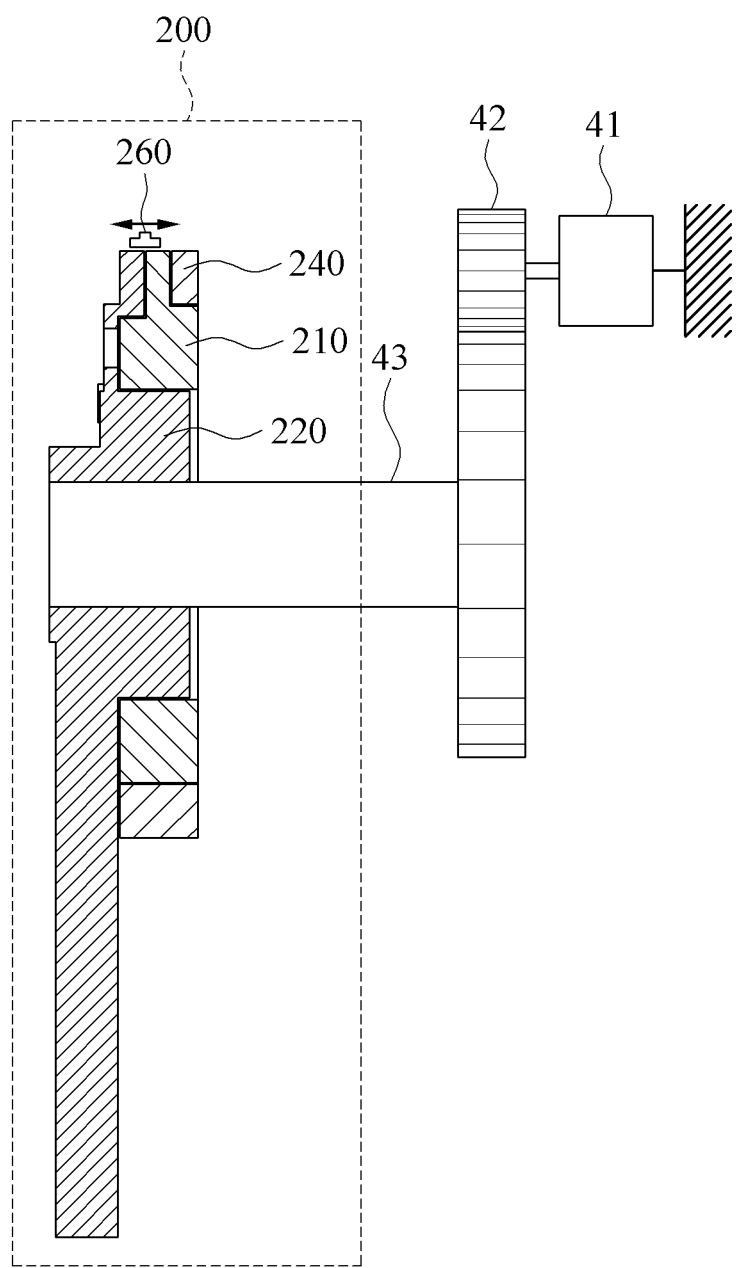
FIG. 9 is a side cross-sectional view illustrating a joint assembly according to at least one example embodiment.

FIG. 9 is a side cross-sectional view of a joint assembly according to at least one example embodiment.

Referring to FIG. 9, a binder 260 may selectively fix the profile ring 210 to one of the rotor 220 and the fixed ring 240.

Figure 10A:
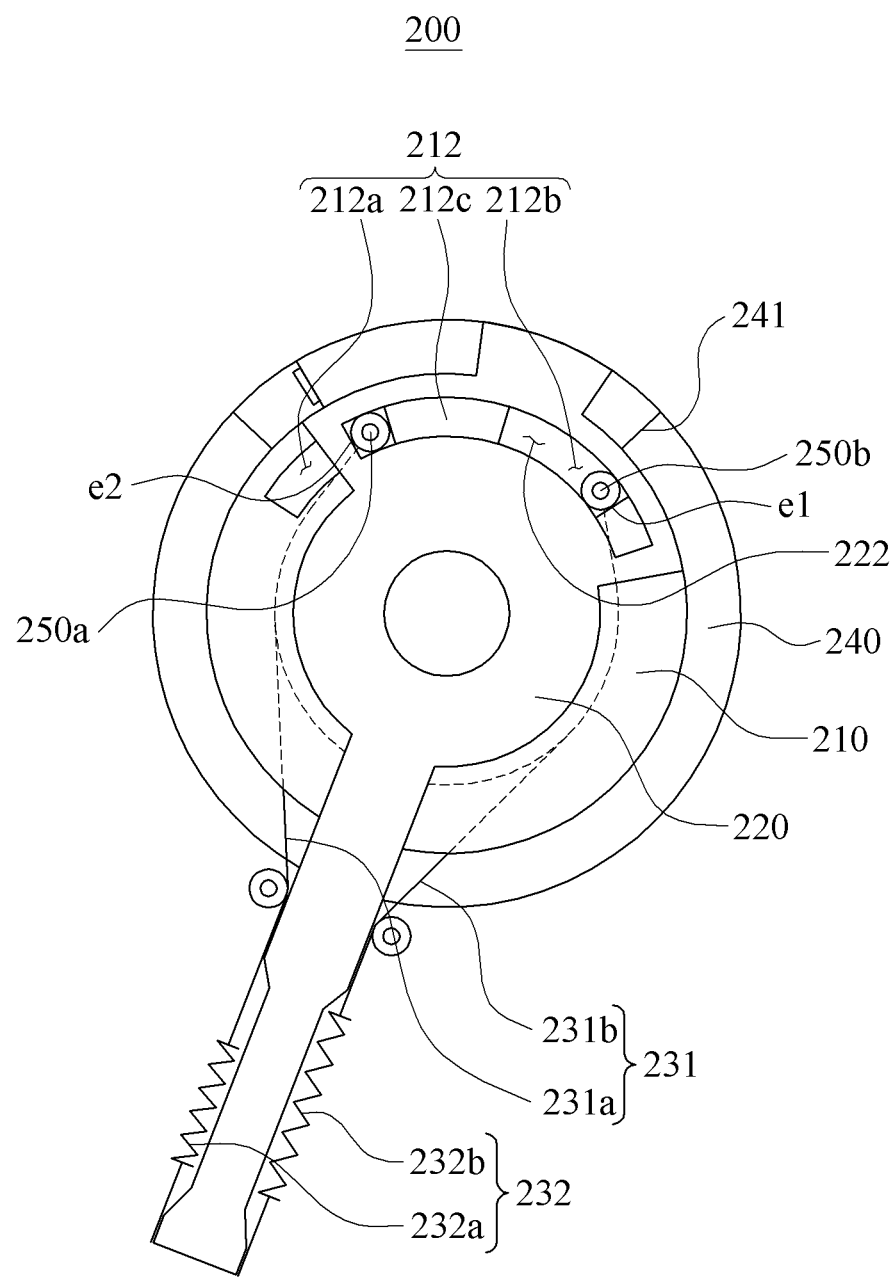
FIGS. 10A and 10B are top views to describe an operation form of a joint assembly in response to an operation of a binder according to at least one example embodiment.
Figure 10B:
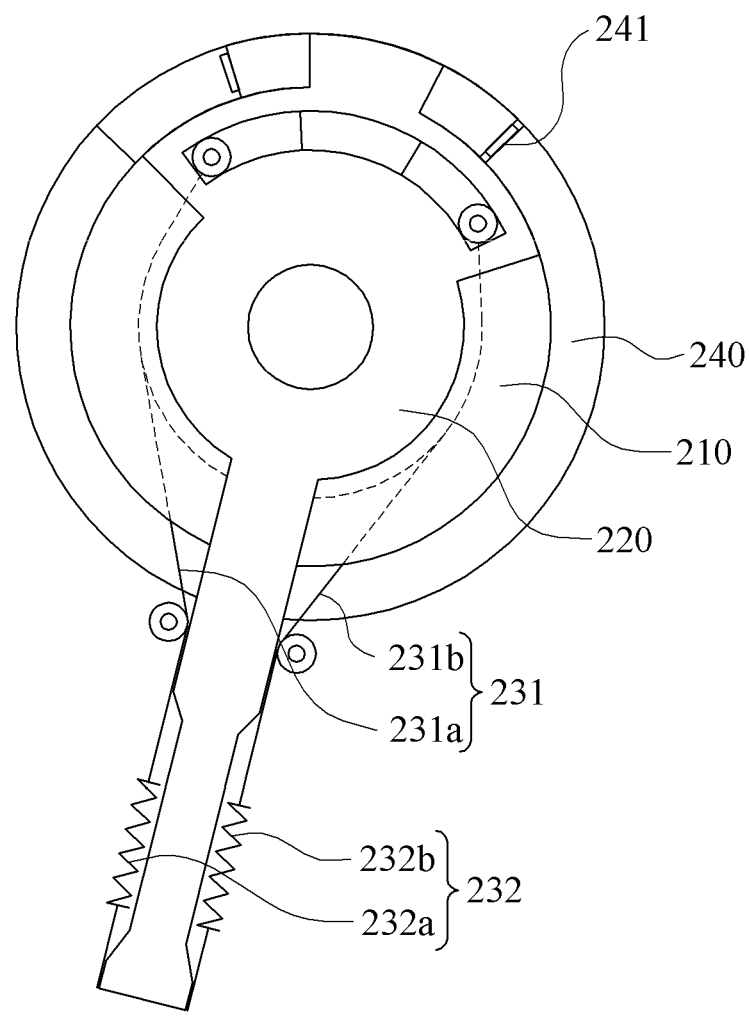

FIGS. 10A and 10B are top views to describe an operation form of a joint assembly in response to an operation of a binder according to at least one example embodiment.

FIG. 10A illustrates an operation of the joint assembly 200 in a state in which the binder 260 fixes the profile ring 210 to the fixed ring 240, and FIG. 10 B illustrates an operation of the joint assembly 200 in a state in which the binder 260 fixes the profile ring 210 to the rotor 220.

Referring to FIGS. 8A and 10A, when the profile ring 210 is fixed to the fixed ring 240 by the binder 260, the rotor 220 may rotate relative to the profile ring 210. Hereinafter, an example in which the rotor 220 rotates clockwise will be described.

As illustrated in FIG. 8A, initially, the cable holder 250 may be positioned on both sides of the slack prevention slot 222.

As illustrated in FIG. 10A, the rotor 220 may start rotating and in this instance, the second cable holder 250b and the rotor 220 may rotate together until the second cable holder 250b becomes in contact with one end e1 of the second guide slot 212b. Thus, the second elastic body 232b may not extend.

That is, the above section corresponds to a free rotation section in which the elastic potential energy of the second elastic body 232b does not vary despite of the rotation of the rotor 220.

Since a position of the first cable holder 250a is fixed at an end e2 of the slack prevention slot 222, the first cable 231a and/or the first elastic body 232a may not become slack.

When the rotor 220 additionally rotates in a state in which the second cable holder 250b is positioned at the one end e1 of the second guide slot 212b, the profile ring 210 may not rotate and thus, the rotor 220 may rotate in a state in which a position of the second cable holder 250b is fixed to the end e1 of the second guide slot 212b. Accordingly, the second elastic body 232b may extend, thereby increasing the elastic potential energy of the second elastic body 232b.

A maximum rotation angle of the rotor 220 may be determined based on the first guide slot 212a or the stopper 241. For example, when a portion of the rotor 220 is in contact with the stopper 241, rotation of the rotor 220 may be limited.

Alternatively, when the rotor 220 rotates and the first cable holder 250a becomes in contact with the separator 212c accordingly, the rotation of the rotor 220 may receive interference by way of the fixed profile ring 220. Thus, the rotation of the rotor 220 may be limited.

Accordingly, it is possible to limit a rotation radius of the rotor 220 by adjusting a length of the stopper 241 or the guide slot 212.

The joint assembly 200 configured as above may be used in the aforementioned hybrid assistance mode or passive assistance mode.

Referring to FIG. 10B, when the profile ring 210 is fixed to the rotor 220 by the binder 260, the rotor 220 may rotate together with the profile ring 210.

For example, the rotor 220 and the profile ring 210 may rotate together relative to the fixed ring 240, according to a motion of a joint of the user. Hereinafter, an example in which the rotor 220 rotates clockwise will be described.

When the rotor 220 and the profile ring 210 rotate together, a length of the cable 231 and a length of the elastic body 232 may not vary. That is, since the length of the cable 231 and the length of the elastic body 232 are maintained regardless of rotation of the rotor 220, the elastic potential energy of the elastic body 232 may not vary. A rotation angle of the rotor 220 may be limited by the stopper 241.

The joint assembly 200 configured as above may be used in the aforementioned active assistance mode or free mode.

Figure 11A:
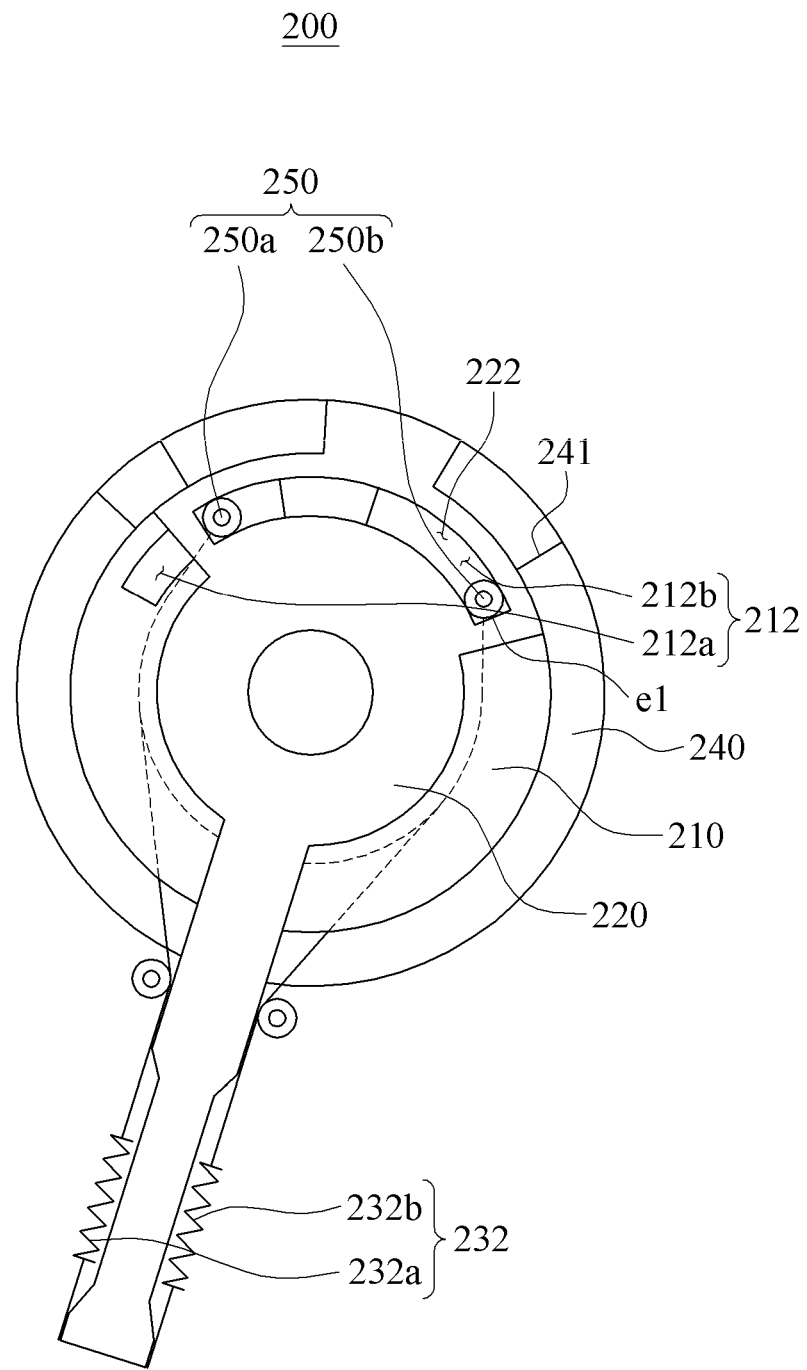
FIGS. 11A, 11B, and 11C are top views to describe an operation form of a joint assembly in which a binder is absent according to at least one example embodiment.
Figure 11B:
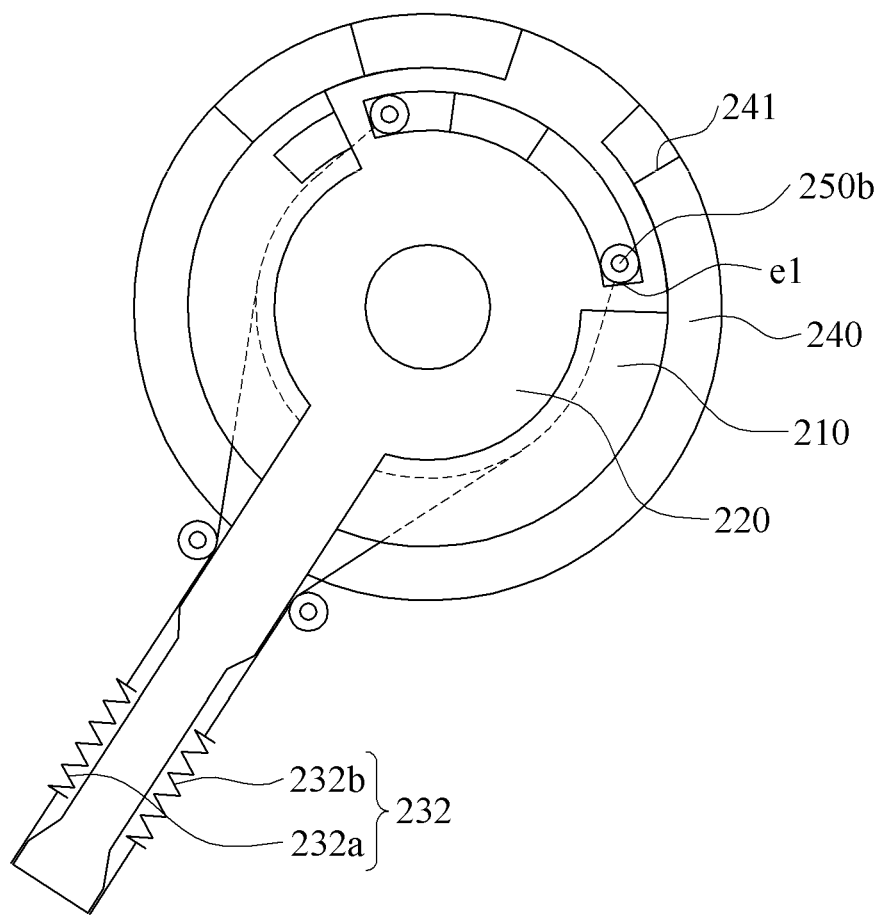
Figure 11C:
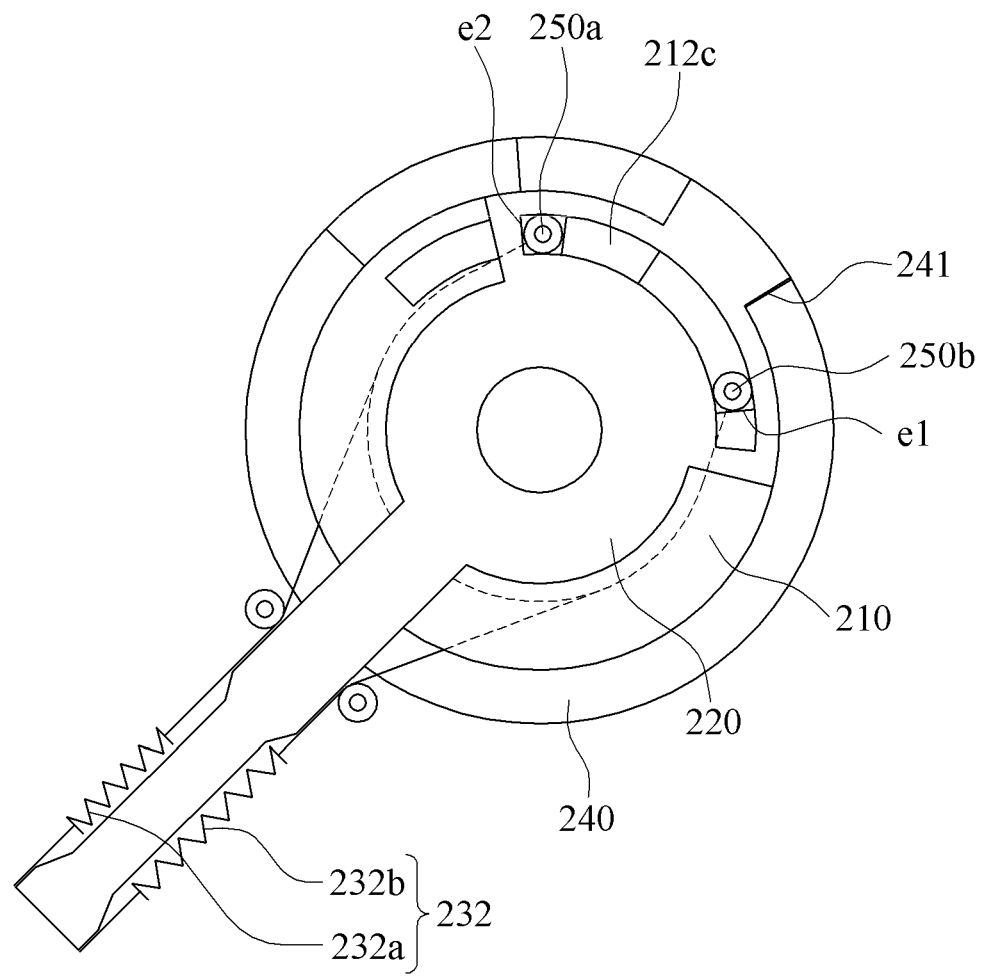

FIGS. 11A, 11B, and 11C are top views to describe an operation form of a joint assembly in which a binder is absent according to at least one example embodiment.

FIG. 11A illustrates an example in which the rotor 220 rotates, FIG. 11B illustrates an example in which the rotor 220 and the profile ring 210 rotate together, and FIG. 11C illustrates an example in which the rotor 220 rotates, thereby changing the elastic potential energy of the elastic body 232.

Referring to FIGS. 11A, 11B, and 11C, the joint assembly 200 may include the rotor 220, the profile ring 210, and the fixed ring 240. The rotor 220 may rotate relative to the profile ring 210, and the profile ring 210 may rotate relative to the fixed ring 240.

Depending on a rotation level of the rotor 220, the rotor 220 alone may rotate, the rotor 220 and the profile ring 210 may rotate together, or the rotor 220 alone may rotate and thereby change the elastic potential energy of the elastic body 232.

Hereinafter, an example in which the rotor 220 rotates clockwise will be described.

Referring to FIGS. 8A and 11A, the rotor 220 may rotate from the initial position of FIG. 8A. Due to the elastic force, the first cable holder 250a and the second cable holder 250b may be positioned at both sides of the slack prevention slot 222, respectively. Positions of the first cable holder 250a and the second cable holder 250b may be fixed due to the elastic force.

The rotor 220 may rotate alone until the second cable holder 250b becomes in contact with an end of the guide slot 212. In this state, the elastic potential energy may not vary. FIG. 11A illustrates a state in which the rotor 220 rotates and the second cable holder 250b is positioned at the end e1 of the second guide slot 212b. In this instance, the end e1 of the second guide slot 212b may be positioned on the same line as the end of the slack prevention slot 222.

Referring to FIG. 11B, the rotor 220 may additionally rotate from the position of FIG. 11A. The second cable holder 250b may press the profile ring 210 at the end e1 of the second guide slot 212b whereby the rotor 220 may rotate together with the profile ring 210.

That is, a position of the second cable holder 250b may be fixed at the end of the slack prevention slot 222 due to the elastic force. When the end of the slack prevention slot 222 and the end e1 of the second guide slot 212b are positioned on the same line, the second cable holder 250b may rotate the profile ring 210.

As illustrated in FIG. 11B, the stopper 241 may contact the profile ring 210 to interfere with rotation of the profile ring 210. That is, the stopper 241 may limit a rotation angle of the profile ring 210.

Referring to FIG. 11C, the rotor 220 may further rotate from the position of FIG. 11B whereby the second elastic body 232b may extend and the elastic potential energy may vary.

In detail, the second cable holder 250b may be positioned at the end e1 of the second guide slot 212b and the slack prevention slot 222, a position of the profile ring 210 is fixed by the stopper 241 and thus, the position of the second cable holder 250b may be fixed at the end e1 of the second guide slot 212b.

When the rotor 220 additionally rotates in this state, a distance from the second cable holder 250b to one side of the extending body 220b may increase whereby the elastic body 232 may extend and the elastic potential energy may increase.

As illustrated in FIG. 11C, when the second cable 231b is maximally extended, the first cable holder 250a may come into contact with the separator 212c and a portion of the rotor 220 may come into contact with the stopper 241 such that the rotor 220 is restricted from further rotating.

As illustrated in FIGS. 11A to 11C, while the rotor 220 rotates clockwise, the first cable holder 250a may be positioned at the end of the slack prevention slot 222 at all times. Accordingly, it may be possible to prevent the first cable 231a or the first elastic body 232a from becoming slack.

Figure 12:
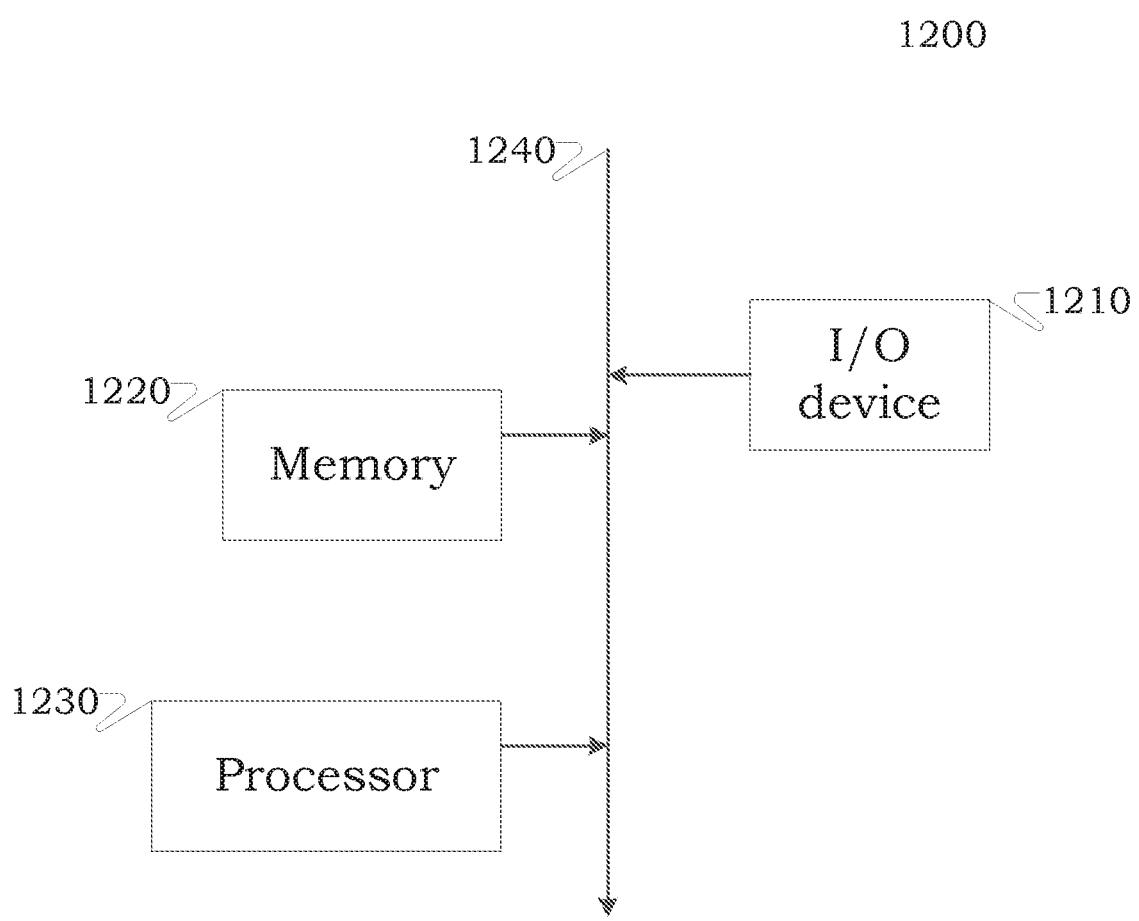
FIG. 12 illustrates a controller according to example embodiments.

FIG. 12 illustrates a controller according to example embodiments.

Referring to FIG. 12, a controller 1200 may include a memory 1210, a processor 1220, an input/output (I/O) device 1230, and a bus 1240 connecting same. The controller 1200 may be mounted on, for example, the fixing module 20.

The I/O device 1210 may include transmitters and/or receivers. The transmitters may include hardware and any necessary software for transmitting signals including, for example, data signals and/or control signals to the driver 40 and/or the joint assembly 10. The receivers may include hardware and any necessary software for receiving signals including, for example, data signals and/or control signals from one or more sensors.

The memory 1220 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor 1230 may be implemented by at least one semiconductor chip disposed on a printed circuit board. The processor 1230 may be an arithmetic logic unit, a digital signal processor, a microcomputer, a field programmable array, a programmable logic unit, a microprocessor or any other device capable of responding to and executing instructions in a defined manner.

The processor 1230 may be programmed with instructions that configure the processor 1230 into a special purpose computer to perform the operations illustrated in one or more of FIGS. 13 and 14, discussed below, such that the processor 1230 is configured to switch the operating mode of the motion assistance device 1.

For example, the processor 1230 may transmit, via the I/O device 1210, control instructions to control the driver 40 and/or the joint assembly 10 based on information provided by the sensors. For example, the processor 1230 may transmit control instructions to the joint assembly 10 and/or the driving module 40 to switch the operating mode of the motion assistance device 1 between the passive assistance mode, the active assistance mode, the hybrid assistance mode, and the free mode based on, for example, the signals provided by one or more of the sensors and/or an input received by the user.

Further, in some example embodiments, the processor 1230 may receive, via the I/O device 1210, the signals from the one or more sensors including information associated with a movement of the wearer. For example, the sensors may be pressure sensors located on a sole of the wearer, potentiometer that senses joint angles or joint angular velocities, or an inertial measurement unit (IMU) sensor that measures acceleration information while the user is ambulatory. The processor 1230 may determine that the wearer is walking with difficulty, for example, that the wearer is moving slower than a normal pace associated with the wearer, based on the information from the sensors, and transmit the control instructions to the joint assembly 10 and/or the driving module 40 to switch the operating mode from one of the free mode and the passive assistance mode to one of the active assistance mode, the hybrid assistance mode, if the user is experiencing difficulty walking.

Figure 13:
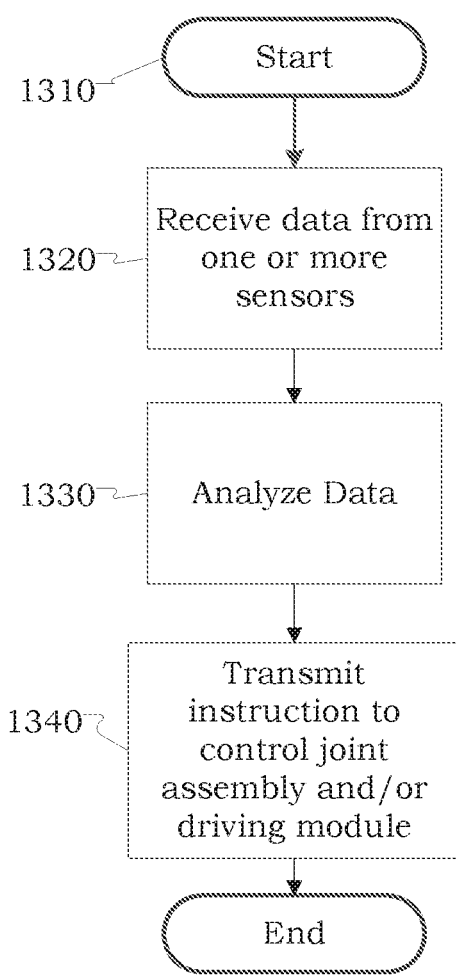
FIGS. 13 and 14 illustrate methods of controlling a motion assistance apparatus according to example embodiments.

FIG. 13 illustrates a method of controlling a motion assistance apparatus according to example embodiments.

Referring to FIG. 13, in operation 1310 the controller 1200 may initialize.

In operation 1320, the controller 1200 may receive data from one or more sensors. For example, the controller 1200 may receive the data from the sensors via the I/O device 1210.

In operation 1330, the controller 1200 may analyze the data to determine a desired operating mode of the joint assembly 10 and/or the driving module 40. Details on the determination of the desired operating mode are discussed below with reference to FIG. 14.

In operation 1340, the controller 1200 may transmit one or more instruction to control the joint assembly 10 and/or the driving module 40 based on the desired operating mode. For example, the controller 1200 may transmit, via the I/O deice 1210, an instruction to the joint assembly 10 and/or the driving module 40 to set the motion assistance device 1 into one of the passive assistance mode, the active assistance mode, the hybrid assistance mode, and the free mode based on the desired operating mode.

Figure 14:
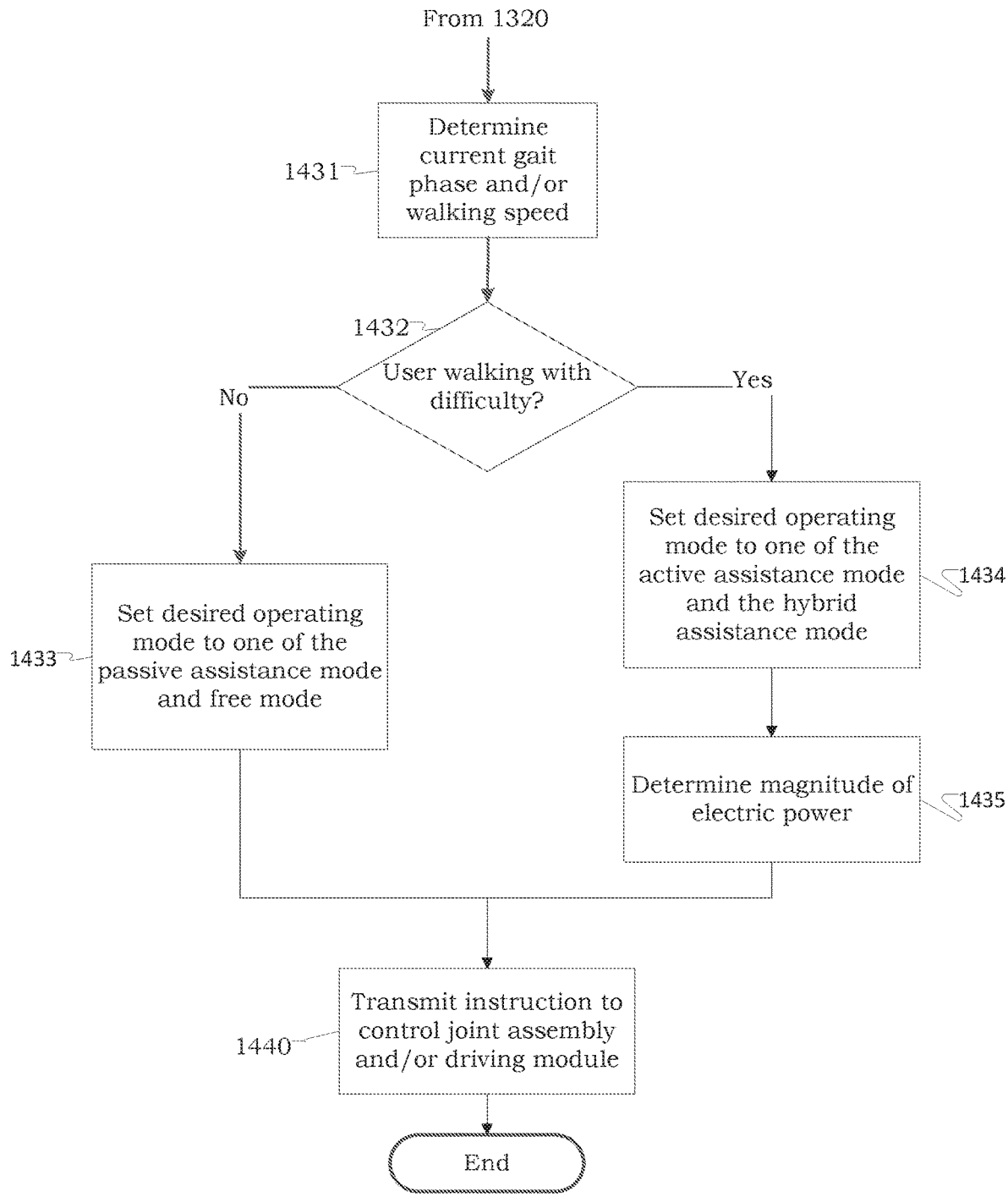

FIG. 14 illustrates a method of controlling a motion assistance apparatus according to example embodiments.

Referring to FIG. 14, in operation 1431, the controller 1200 may determine a current gait phase of a gait cycle of the user and/or a walking speed of the user based on information from the sensors.

In operation 1432, the controller 1200 may determine may determine whether the user is walking with difficulty based on the data received from the sensors in operation 1320, the current gait phase and/or the walking speed of the user.

If, in operation 1432, the controller 1200 determines that the user is not walking with difficulty, in operation 1433, the controller 1200 may determine that the desired operating mode is one of a passive assistance mode and a free mode such that power consumption is reduced due the controller 1200 not driving the actuator 41.

If, in operation 1432, the controller 1200 determines that the user is walking with difficulty, in operation 1434, the controller 1200 may determine that the desired operating mode is one of the active assistance mode and the hybrid assistance mode such that the elastic assistance force $T_p$ or both the elastic assistance force $T_p$ and the electric power $T_a$ from the actuator 41 are supplied to the joint assembly 10, respectively.

In operation 1435, the controller 1200 may determine a magnitude of the power supplied by the actuator 41 in the active assistance mode or the hybrid assistance mode based on, for example, the walking speed of the user.

In operation 1440, the controller 1200 may transmit one or more instructions to the joint assembly 10 and/or the driving module 40 based on the desired operating mode and/or the walking speed of the user.

In response to the instruction from the controller 1200, the actuator 41 may selectively transmit the electric power and/or an actuator connected to the binder 150 may set the binder 150 to the first position or the second position to put the motion assistance apparatus in the desired operating mode.

When operating in the passive assistance mode or the hybrid assistance mode, due to the design of the cam profile, a magnitude of the elastic assistance force $T_p$ may vary based on a rotation of the rotor 120 such that, for example, the elastic assistance force increases proportionally with respect to an amount of extension and/or flexion of the joint of the user. Further, when operating in the active assistance mode or the hybrid assistance mode, the magnitude of the power supplied by the actuator 41 may vary based on the walking speed of the user.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A joint assembly comprising:
   a profile ring including a cam profile;
   a rotor configured to rotate relative to the profile ring;
   an elastic body connected to the rotor, the elastic body configured to store an elastic potential energy in response to the rotor rotating relative to the profile ring such that the elastic potential energy corresponds to a shape of the cam profile;
   a fixed ring enclosing the profile ring such that the profile ring selectively rotates relative thereto; and
   a binder configured to move between a first position coupling the profile ring to the rotor while disconnecting the profile ring from the fixed ring, and a second position coupling the profile ring to the fixed ring while disconnecting the profile ring from the rotor.

2. The joint assembly of claim 1, wherein,
   the rotor is configured to rotate relative to the profile ring such that the elastic potential energy of the elastic body varies, in response to the binder coupling the profile ring to the fixed ring, and
   the rotor and the profile ring are configured to rotate as a single rigid body such that the elastic potential energy of the elastic body is static, in response to the binder coupling the profile ring to the rotor.

3. The joint assembly of claim 1, further comprising:
   a pressurizing portion connected to a first end of the elastic body; and
   a roller connected to the pressurizing portion, the roller configured to contact the cam profile with an elastic force generated by the elastic body.

4. The joint assembly of claim 3, wherein
the elastic body includes a first elastic body and a second elastic body, the first elastic body and the second elastic body connected to a first end and a second end of a first surface of the pressurizing portion, respectively, with a center of rotation of the rotor therebetween.

5. The joint assembly of claim 3, wherein a second end of the elastic body is within a cylinder hole in the rotor, and the joint assembly further comprises:
a friction reduction member between a side surface of the elastic body and an inner surface of the cylinder hole, the friction reducing member configured to reduce friction between the elastic body and the rotor.

6. The joint assembly of claim 3, wherein the rotor is configured to rotate such that a distance from a center of rotation of the rotor to an end of the roller is maximum when the rotor in an initial state.

7. The joint assembly of claim 3, wherein the shape of the cam profile is such that a distance from a center of rotation of the rotor to a portion of the cam profile is less than or equal to a minimum distance from the center of rotation of the rotor to an end of the roller.

8. The joint assembly of claim 1, wherein the shape of the cam profile is such that both sides of the cam profile relative to an initial position of the rotor are asymmetric.

9. A joint assembly comprising:
a profile ring including a cam profile;
a rotor configured to rotate relative to the profile ring;
a cable configured to wind around the cam profile in response to rotation of the rotor;
an elastic body connected to the cable, the elastic body configured to store an elastic potential energy in response to winding of the cable;
a fixed ring enclosing the profile ring such that the profile ring rotates relative thereto; and
a binder configured to move between a first position coupling the profile ring to a first one of the rotor and the fixed ring while disconnecting the profile ring from a second one of the rotor and the fixed ring, and a second position coupling the profile ring to the second one of the rotor and the fixed ring while disconnecting the profile ring from the first one of the rotor and the fixing ring.

10. The joint assembly of claim 9, wherein,
the rotor is configured to rotate relative to the profile ring such that the cable is wound around the cam profile to vary the elastic potential energy of the elastic body, in response to the binder coupling the profile ring to the fixed ring, and
the rotor and the profile ring are configured to rotate as a single rigid body such that the elastic potential energy of the elastic body is static, in response to the binder coupling the profile ring to the rotor.

11. The joint assembly of claim 9, wherein the rotor includes a slack prevention slot along a circumference thereof and the profile ring includes a guide slot along a circumference thereof corresponding to the slack prevention slot, and the joint assembly further comprises:
a cable holder connected to one side of the cable, the cable holder configured to move within the guide slot and the slack prevention slot.

12. The joint assembly of claim 11, wherein a length of the guide slot is greater than a length of the slack prevention slot.

13. The joint assembly of claim 11, wherein
the elastic body includes a first elastic body and a second elastic body,
the cable includes a first cable and a second cable, a first end of the first cable and a first end of the second cable connected to the first elastic body and second elastic body, respectively,
the cable holder includes a first cable holder and a second cable holder connected to a second end of the first cable and a second end of the second cable, respectively, and
the guide slot includes a first guide slot and a second guide slot configured to direct the first cable holder and the second cable holder, respectively.

14. The joint assembly of claim 13, wherein the rotor comprises:
a rotary body; and
an extending body extending from the rotary body, the extending body having a first side and a second side, the first elastic body and the second elastic body on the first side and second side of the extending body, respectively.

15. The joint assembly of claim 14, further comprising:
a plurality of idlers adjacent to the extending body,
wherein the cable is wound between the extending body and the idlers to adjust a tension in the cable.

16. The joint assembly of claim 9, further comprising:
a stopper on the fixed ring, the stopper configured to resist rotation of one or more of the rotor and the profile ring, if the rotor or the profile ring contacts the stopper.

17. The joint assembly of claim 9, wherein the cam profile is shaped such that both sides of the cam profile relative to an initial position of the rotor are asymmetric.

18. The joint assembly of claim 9,
wherein
the elastic body is configured to vary the elastic potential energy when the cable winds around the cam profile.

19. The joint assembly of claim 18, wherein the rotor includes a slack prevention slot along a circumference thereof and the profile ring includes a guide slot along a circumference thereof corresponding to the slack prevention slot, and the joint assembly further comprises:
a cable holder connected to one side of the cable, the cable holder configured to move within the guide slot and the slack prevention slot such that, when the cable holder moves to one end of the guide slot, the rotor is configured to rotate together with the profile ring.

20. The joint assembly of claim 19, further comprising:
a stopper on the fixed ring, the stopper configured to resist rotation of one or more of the rotor and the profile ring such that, when the stopper resists the rotation of the profile ring, the rotor is configured to rotate while the profile ring is stationary to vary a magnitude of the elastic potential energy of the elastic body.

* * * * *